United States Patent [19]
Dai et al.

[11] Patent Number: 5,856,588
[45] Date of Patent: Jan. 5, 1999

[54] TWO-STAGE ETHERIFICATION OF TERTIARY BUTYL ALCOHOL USING SECOND STAGE ZEOLITE CATALYSTS FOR THE INTERMEDIATE PREPARATION OF ISOBUTYLENE

[75] Inventors: Pei-Shing Eugene Dai, Port Arthur; John Frederick Knifton, Austin, both of Tex.

[73] Assignee: Huntsman Specialty Chemicals Corporation, Austin, Tex.

[21] Appl. No.: 774,339

[22] Filed: Dec. 30, 1996

Related U.S. Application Data

[63] Continuation-in-part of Ser. No. 338,079, Nov. 14, 1994.
[51] Int. Cl.$^6$ ..................................................... C07C 41/00
[52] U.S. Cl. ............................................. 568/698; 568/671
[58] Field of Search ..................................... 568/698, 671

[56] References Cited

U.S. PATENT DOCUMENTS

| | | | |
|---|---|---|---|
| 5,313,006 | 5/1994 | Knifton | 568/698 |
| 5,386,065 | 1/1995 | Kruse et al. | 568/698 |

*Primary Examiner*—Gary Geist
*Assistant Examiner*—J. Parsa
*Attorney, Agent, or Firm*—Russell R. Stolle; Ron D. Brown; Carl G. Ries

[57] ABSTRACT

Methyl tertiary butyl ether is prepared from tertiary butyl alcohol and methanol in a plural stage process by (a) reacting tertiary butyl alcohol with methanol in a primary MTBE reaction zone containing a cationic ion-exchange resin catalyst to form a primary reaction product, (b) fractionating the primary reaction product in a primary distillation zone to provide a first lighter, lower boiling distillation fraction comprising isobutylene, methanol and methyl tertiary butyl ether and a first heavier, higher boiling distillation fraction comprising methanol, tertiary butyl alcohol and water, c) contacting the first heavier distillation fraction in a second stage reactor containing a second stage acidic, fluoride-treated Y-zeolite having a silica:alumina ratio of 100:1 to 10:1 and a unit cell size of from 24.20 to 24.45 Å or a fluoride-treated silicoaluminophosphate (SAPO) molecular sieve having a pore size of from 5 Å to 8 Å, under conversion conditions including a temperature of from 20° to 300° C. and a pressure of from 0 to 1000 psig to form a second stage reaction product rich in isobutylene and also containing methyl tertiary butyl ether; and (d) converting the isobutylene to additional methyl tertiary butyl ether.

4 Claims, 2 Drawing Sheets

TWO-STAGE ETHERIFICATION OF TERTIARY BUTYL ALCOHOL USING SECOND STAGE ZEOLITE CATALYSTS FOR THE INTERMEDIATE PREPARATION OF ISOBUTYLENE

This application is a continuation-in-part of copending Dai et al. U. S. patent application Ser. No. 08/338,079 filed Nov. 14, 1994 and entitled: "CATALYST FOR MULTI-STAGE ETHERIFICATION WITH HIGH CONVERSION OF t-BUTANOL."

CROSS REFERENCE

This application is related to U.S. Pat. Nos. 5,099,072, 5,169,592 and 5,081,318 and to Ser. No. 07/917,885.

1. Field of the Invention

This invention is directed to a plural stage process for the preparation of methyl tertiary butyl ether from tertiary butyl alcohol and methanol wherein an acidic, fluoride-treated Y-zeolite, or a fluoride-treated silicoaluminophosphate having defined physical characteristics is employed in a second stage reactor to provide a second stage intermediate reaction product rich in isobutylene and also containing methyl tertiary butyl ether. More particularly, this invention is directed to a plural stage process for the preparation of methyl tertiary butyl ether from tertiary butyl alcohol and methanol wherein a feed mixture comprising tertiary butyl alcohol and methanol is reacted in a primary MTBE reaction zone containing a cationic ion-exchange resin catalyst to form a primary reaction product comprising methyl tertiary butyl ether, unreacted tertiary butyl alcohol, unreacted methanol, isobutylene and water; wherein the primary reaction product is fractionated to provide a first lighter, lower boiling distillation fraction comprising isobutylene, methanol and methyl tertiary butyl ether and a first heavier, higher boiling distillation fraction comprising methanol, tertiary butyl alcohol and water and wherein the first heavier distillation containing fraction is charged to a second stage reactor containing an acidic, fluoride-treated Y-zeolite, or a fluoride-treated silicoaluminophosphate having defined physical characteristics to form a second stage reaction product rich in isobutylene and also containing methyl tertiary butyl ether and from which isobutylene and methyl tertiary butyl ether are obtained for further treatment.

In accordance with one embodiment of the present invention, the catalyst that is used in the second stage reactor is an acidic, fluoride-treated Y-zeolite, having defined physical characteristics such as a catalyst comprising strongly acidic Y-zeolites having a silica:alumina ratio of 100:1 to 10:1 and a unit cell size of from 24.20 to 24.45 Å, modified with a fluoride-containing compound.

In another embodiment of the instant invention silicoaluminophosphate (SAPO) molecular sieves may be employed. Suitable SAPOs include, but are not limited to large pore SAPOs, such as, for example, SAPO-37 and SAPO-5 and medium pore SAPOs such as, for example SAPO-11 and SAPO-31, modified with a fluoride-containing compound.

A preferred embodiment of the present invention comprises the preparation of methyl tertiary butyl ether from tertiary butyl alcohol and methanol in plural stages and comprises the steps of:

a. charging a reaction feed mixture comprising methanol and tertiary butyl alcohol to a primary MTBE reaction zone containing a bed of a cationic ion-exchange resins catalyst and reacting the reaction feed mixture therein to form a primary etherification reaction product comprising unreacted methanol, unreacted tertiary butyl alcohol, water, isobutylene and methyl tertiary butyl ether;

b. charging the primary reaction product to a first methyl tertiary butyl ether distillation zone and separating it therein into a first lighter distillation fraction comprising isobutylene, methanol and methyl tertiary butyl ether and a first heavier distillation fraction comprising methanol, tertiary butyl alcohol and water;

c. charging the first heavier distillation fraction to a second stage MTBE reaction zone containing a bed of an acidic, fluoride-treated Y-zeolite, or a fluoride-treated silicoaluminophosphate and reacting the tertiary butyl alcohol and methanol therein to form a second stage etherification reaction product comprising an enhanced quantity of isobutylene and methyl tertiary butyl ether, and also containing unreacted tertiary butyl alcohol, methanol and water;

d. charging the second stage reaction product to a second methyl tertiary butyl ether distillation zone and fractionating it therein to provide a second lighter distillation fraction comprising methanol, tertiary butyl alcohol, isobutylene and methyl tertiary butyl ether, and a second heavier distillation fraction comprising water;

e. recycling the second lighter distillation fraction to the first methyl tertiary butyl ether distillation zone; and f. the fluorine modified zeolite catalyst comprising a strongly acidic Y-zeolite having a silica/alumina ratio of 100:1 to 10:1 and a unit cell size of 24.20 to 24.45 Å, the silicoaluminaphosphate having a pore size of from 5 to 9 Å.

In accordance with another embodiment of the present invention, the process includes the additional steps of:

g. charging the first lower boiling (lighter) distillation fraction and an isobutylene conversion product to a methanol solvent extraction zone and counter-currently contacting them therein with water to provide an overhead extract comprising isobutylene, water and methyl tertiary butyl ether and a raffinate comprising methanol, MTBE, isobutylene, dimethyl ether and water;

h. charging the extract to a third isobutylene distillation zone and separating it therein into a third lower boiling (lighter) distillation fraction comprising isobutylene, a third intermediate boiling fraction comprising water, and a third higher boiling (heavier) distillation fraction comprising methyl tertiary butyl ether;

i. charging at least a portion of the third lighter isobutylene fraction and added methanol to an isobutylene conversion reaction zone containing a bed of a cationic ion-exchange resin catalyst and reacting the reaction feed mixture therein to thereby convert the charged methanol and isobutylene to methyl tertiary butyl ether and form an isobutylene conversion product comprising methyl tertiary butyl ether, isobutylene, methanol, tertiary butyl alcohol and water; and j. recycling said isobutylene conversion product to said methanol solvent extraction zone.

2. Prior Art

Knifton et al. U.S. Pat. No. 5,183,947 discloses a method for reacting tertiary butyl alcohol with methanol in the presence of a montmorillonite clay treated with fluorophosphoric acid.

Knifton U.S. Pat. No. 5,214,217 discloses a method for reacting tertiary butyl alcohol with methanol in the presence of acidic aluminas or crystalline aluminosilicate faujasite-type zeolites, particularly dealuminized Y-type zeolites.

Knifton et al. U.S. Pat. No. 5,300,697 discloses a method for reacting tertiary butyl alcohol with methanol in the presence of a crystalline aluminosilicate faujasite-type zeolite modified with hydrogen fluoride.

Knifton U.S. Pat. No. 5,313,006 discloses a two-step process for reacting tertiary butyl alcohol with methanol where the reaction product of the first step is fractionated to provide a bottoms fraction that is etherified in the presence of a crystalline aluminosilicate faujasite-type zeolite modified with a fluoride-containing compound.

Kruse et al. U.S. Pat. No. 5,386,065 discloses a two-step process for reacting tertiary butyl alcohol with methanol where the reaction product of the first step is fractionated to provide a bottoms fraction that is etherified in the presence of an acidic etherification catalyst.

Kruse et al. U.S. Pat. No. 5,386,065 discloses a two-step process for reacting tertiary butyl alcohol with methanol where the reaction product of the first step is fractionated to provide an isobutylene fraction that is etherified in the presence of an acidic etherification catalyst.

Knifton et al. U.S. Pat. No. 5,387,722 discloses a method for reacting tertiary butyl alcohol with methanol in the presence of a pentasil.

Knifton et al. U.S. Pat. No. 5,387,723 discloses a method for reacting tertiary butyl alcohol with methanol in the presence of a modified beta zeolite.

BACKGROUND OF THE INVENTION

Methyl tert-butyl ether is finding increasing use as a blending component in high octane gasoline as the current gasoline additives based on lead and manganese are phased out. Currently most commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, October 1984, p. 63; Oil and Gas J., Jan. 1, 1979, p. 76; Chem. Economics Handbook-SRI, September 1986, p. 543-7051P). The cationic ion-exchange resins used in MTBE synthesis normally have the sulfonic acid functionality (see: J. Tejero, J. Mol. Catal., 42 (1987) 257; C. Subramamam et al., Can. J. Chem. Eng., 65 (1987) 613).

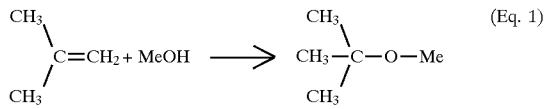

The dehydration reaction can be represented by:

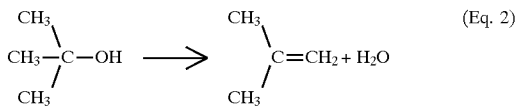

With the expanding use of MTBE as an acceptable gasoline additive, a growing problem is the availability of raw materials. Historically, the critical raw material has been isobutylene (Oil and Gas J., Jun. 8, 1987, p. 55), however, recently, U.S. Pat. Nos. 5,099,072, 5,169,592 and 5,081,318, inter alia, assigned to Texaco Chemical Inc., disclose a one-step method for producing methyl tert-butyl ether (MTBE) from t-butanol (tBA) over various catalysts. It would be advantageous to obtain additional conversion of the t-butanol in the crude feedstock without having to recycle unconverted tertiary butanol.

"Preparation of Methyl Tert-Butyl Ether (MTBE) Over Zeolite Catalysts" is an article by Pochen Chu and Günther H. Kühl, Ind. Eng. Chem. Res., 26, 365, 1987. Chu et al. disclose work which identifies ZSM-5 and ZSM-11 to be selective for the preparation of MTBE. Compared to the conventional Amberlyst 15 resin, the zeolites are thermally stable, and give no acid effluent; they provide high selectivity to MTBE with little or no diisobutene yield, are less sensitive to the $CH_3OH/i\text{-}C_4H_8$ ratio and exhibit good selectivity even at ratios approaching unity. They provide high MTBE output, despite the unfavorable thermodynamic equilibrium, since the process utilizing these zeolites can be operated at high temperature and high space velocity. In addition, deactivation is not observed in the present short catalytic tests and reactivation is not required. The excellent selectivity of these two zeolites is believed to be effected by the size of their pore structure, which provides easy access to methanol and restricted access to isobutene. Zeolite beta was also tested, giving the poorest results and small pore zeolites were inactive. As expected, large pore zeolites did not exhibit shape selectivity.

An extensive body of knowledge of zeolite properties and catalytic potential has developed in recent years. Different types of zeolites are known in the art, including natural and synthetic zeolites. Research has opened up a spectrum of new opportunities in the field of molecular shape selective catalysis, where the intracrystalline space accessible to molecules has dimensions near those of the molecules themselves. This field is discussed in an article titled "Molecular Shape Selective Catalysis", P. B. Weisz, New Horizons in Catalysis, Part A, 1980. For example, it is possible to catalyze the dehydration of n-butanol over a Linde 5 Å zeolite without reacting isobutanol which may be present. Such research has led to the concept of molecular engineering.

Another good reference for familiarization with the relationship between molecular shapes, structures of zeolites and selectivity for certain catalysis is an article titled "Industrial Application of Shape Selective Catalysis", N. Y. Chen et al., Catal. Rev.-Sci. Eng., 28 185 (1986).

The zeolites of interest for shape-selective catalysis may be divided into three major groups according to their pore/channel systems. The first group includes 8-membered oxygen ring systems such as, for example, Linde A, erionite, chabazite, zeolite alpha, ZK-4, ZK-21, ZK-22 and several other less common natural zeolites.

The second group includes 10-membered oxygen ring systems such as, for example, ZSM-5, ZSM-11, ZSM-22, ZSM-23, ZSM-48 and laumontite, which has a puckered 10-membered oxygen ring. The rest of the medium pore zeolites are usually synthetic in origin; they are sometimes known as pentasils. They have a predominance of silicon.

The third group of zeolites is those having dual pore systems which have interconnecting channels of 12- and 8-membered oxygen ring openings. Examples include mordenite, offretite, clinoptilolite, ferrierite, etc.

In an article titled "Clays, Zeolites and other Microporous Solids for Organic Synthesis," by John M. Thomas et al., in Modern Synthetic Methods, 1989, Vol. 5, p. 249, it is stated at page 263 that the valency or the size of the exchangeable cation can be adjusted, thus fine-tuning the molecular sieving and shape-selective properties. For example, in the $Na^+$ form of zeolite-alpha, the effective void space within the zeolite can be enlarged by replacement of $Na^+$ by $Ca^{2+}$ ions.

Dealumination of a zeolite can enhance the meso-porosity of a zeolite by increasing the Si/Al ratio of the anionic framework and can be represented by the following:

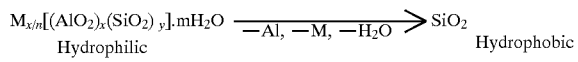
$$M_{x/n}[(AlO_2)_x(SiO_2)_y].mH_2O \xrightarrow{-Al,\ -M,\ -H_2O} SiO_2$$
Hydrophilic → Hydrophobic Hydrothermal treatment will result in ultra-stabilization of the zeolite and recent work indicates Si:Al ratios can be increased to greater than 1000.

In addition to Y-zeolites, silicoaluminophosphates (SAPOs) are useful in the instant invention. SAPOs are one type of new materials to which increasing attention has been devoted recently. These materials include: aluminophosphate-based molecular sieves (AlPO$_4$-n), silicoaluminophosphates (SAPO-n), and metal-containing aluminophosphates (MeAPO-n and MeAPSO-n).

The AlPO$_4$ molecular sieves exhibit an invariant framework composition with an Al/P atomic ratio of 1 and a wide structural diversity. Their product composition expressed as an oxide formula, is xR.Al$_2$O$_3$.1.0∓0.2P$_2$O$_5$.yH$_2$O, where R is an amine or quaternary ammonium template, and x, and y represent the amounts needed to fill the microporous voids. Upon calcination at temperatures of 773–873 K, the molecular sieves are expressed as AlPO$_4$ or a TO2 formula of (Al$_{0.50}$P$_{0.50}$)O$_2$. The microporous AlPO$_4$ materials have novel structures, 5, 11, 14, 16, 18, 31, and 33. For example, the as-synthesized ALPO$_4$-11 has a typical composition of 1.0 Pr$_2$ NH:1.0 Al$_2$O$_3$:1.0 P$_2$O$_5$: 4O H$_2$ and consists of an open framework containing unidimensional 10-ring channels (3.9×6.3 Å).

The major structures crystallized in the new generations of AlPO$_4$-based molecular sieves include at least 30 stable three-dimensional novel structures. Some are topological analogs of zeolites such as faujasite, A, chabazite and erionite.

The materials are classified into binary, ternary, and quaternary compositions based on the number of elements contained in the cationic framework sites of any given structure. Classes of these materials comprise compositions crystallized in the AlPO$_4$, silicoaluminophosphates (SAPO), metal aluminophosphates (MeAPO) and non-metal element incorporated aluminophosphates (ElAPO) families.

SAPO molecular sieves were first reported by Lok et al. (U.S. Pat. No. 4,440,871). SAPO are defined as silicoaluminophosphates with the following general chemical formula

$$nR.(Si_x\ Al_y\ P_z)O_2.bH_2O$$

where R=organic compound and x+y+z=1. They involve a three-dimensional arrangement of SiO$_4$, PO$_4$, and AlO$_4$ tetrahedral connected through shared oxygen atoms. This arrangement results in an open structure containing channels and cages with near atomic dimensions. The structures include large-pore (7–8 Å), medium-pore (~6 Å) and small pore (3–4 Å) materials. The silicoaluminophosphates (SAPO) are made by the substitution of silicon for phosphorus and with some substitution of two silicons for an aluminum plus phosphorus into a hypothetical aluminophosphate framework. The general formula of the anhydrous SAPO composition is 0–0.3R (Si$_x$Al$_y$P$_z$)O$_2$ where the mole fraction of silicon, x, typically varies from 0.04 to 0.20 depending on synthesis conditions and structure type. The typical SAPO-11 framework composition is (Si$_{0.14}$Al$_{0.44}$P$_{0.42}$)O$_2$ with (x+z) greater than y.

More than 40 distinct species of zeolite materials have been identified and there are at least 130 synthetic species. The pore sizes and compositions of typical commercially available zeolites are shown in Table A.

TABLE A

COMMERCIALLY AVAILABLE ZEOLITES

| | | Composition | | Sorption Capacity (wt %) | | |
|---|---|---|---|---|---|---|
| Zeolite | Pore Size/nm | Si/Al | Cation | H$_2$O | nC$_6$H$_{14}$ | C$_6$H$_{12}$ |
| Faujasite | | | | | | |
| X | 0.74 | 1–1.5 | Na | 28 | 14.5 | 16.6 |
| Y | 0.74 | 1.5–3 | Na | 26 | 18.1 | 19.5 |
| US-Y | 0.74 | >3 | H | 11 | 15.8 | 18.3 |
| A | 0.3 | 1.0 | K,Na | 22 | 0 | 0 |
| A | 0.4 | 1.0 | Na | 23 | 0 | 0 |
| A | 0.45 | 1.0 | Ca,Na | 23 | 12.5 | 0 |
| Chabazite | 0.4 | 4 | * | 15 | 6.7 | 1 |
| Clinoptilite | 0.4 × 0.5 | 5.5 | * | 10 | 1.8 | 0 |
| Erionite | 0.38 | 4 | * | 9 | 2.4 | 0 |
| Ferrierite | 0.55 × 0.48 | 5–10 | H | 10 | 2.1 | 1.3 |
| L-type | 0.6 | 3–3.5 | K | 12 | 8 | 7.4 |
| Mazzite | 0.58 | 3.4 | Na,H | 11 | 4.3 | 4.1 |
| Mordenite | 0.6 × 0.7 | 5.5 | * | 6 | 2.1 | 2.1 |
| Mordenite | 0.6 × 0.7 | 5–6 | Na | 14 | 4.0 | 4.5 |
| Mordenite | 0.6 × 0.7 | 5–10 | H | 12 | 4.2 | 7.5 |
| Offretite | 0.58 | 4 | K,H | 13 | 5.7 | 2.0 |
| Phillipsite | 0.3 | 2 | * | 15 | 1.3 | 0 |
| Silicalite | 0.55 | ** | H | 1 | 10.1 | |
| ZSM-5 | 0.55 | 10–500 | H | 4 | 12.4 | 5.9 |

*Denotes a mineral zeolite: cations variable, but usually Na, K, Ca, Mg
**Very large Si:Al Another important aspect regarding zeolites involves methods of generating acidity. Several ways of introducing acidity into a zeolite are known in the art and they result in the formation of Bronsted acid sites. The total acidity of a zeolite catalyst depends on both the concentration of acidic sites and the strength of the individual sites. The number and nature of active sites in a zeolite catalyst can be determined in several ways, including $^{27}Al$ solid state NMR, uptake of base and poisoning experiments. Maximum overall acidity is often found for Si/Al ratios in the range of 5 to 20. Bronsted acid sites formed by various methods can form Lewis acid sites by dehydroxylation:

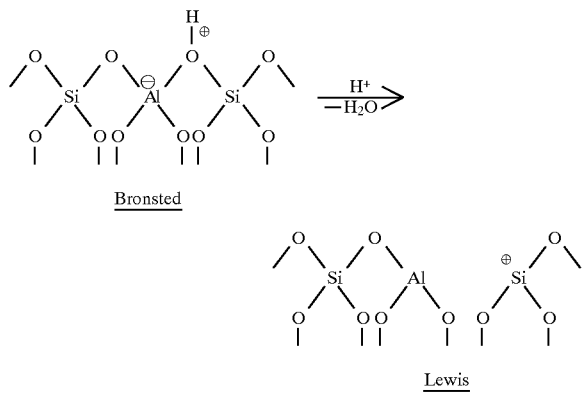

Where shape selectivity by size exclusion is the key to zeolite function, it can be accomplished either through reactant selectivity or product selectivity. It is believed Columbic field effects may also play a part. Another phenomenon which has been observed to contribute is configurational diffusion which occurs in situations where structural dimensions of the catalyst approach those of molecules; even subtle changes in dimensions of molecules can result in large changes in diffusivity, see Chen et al., Catal. Rev.-Sci. Eng., supra, p. 198.

Another type of selectivity which has been observed is spatiospecificity or restricted transition state, where both the reactant molecule and the product molecule are small enough to diffuse through channels, but the reaction intermediates are larger than either the reactants or the products and are spatially constrained.

Reactants which are of particular interest in shape selective catalysis include straight-chain and slightly branched paraffins and olefins, naphthenes and aromatics.

In U.S. Pat. No. 4,943,545, to Chang et al., there is suggested modification of Y-zeolites having Si:Al ratio of at least 4 with a very dilute (0.001→0.1N) solution of HF in a cracking catalyst as a means of reactivation.

In U.S. Pat. No. 5,300,697 there is disclosed a catalyst for synthesis of MTBE from t-BuOH comprising hydrogen fluoride modified zeolites.

In U.S. Pat. No. 5,220,078, there is disclosed a catalyst for MTBE synthesis comprising fluorophosphoric acid-modified zeolites.

In the art, where the feedstock for producing MTBE is t-butanol, the conversions are not as high as would be desirable.

It would be a distinct advance in the art if there were a catalyst available which could withstand sustained operating temperatures of greater than 200° C. and which could be used in a second stage reactor to improve the percentage of conversion of t-butanol to methyl tertiary butyl ether without the necessity of recycling.

It would be a substantial advance in the art if such a catalyst made it possible to obtain greater than 90% conversion of t-butanol, crude t-butanol/methanol feedstocks at low energy cost.

DESCRIPTION OF THE PREFERRED EMBODIMENT

Figure 1:
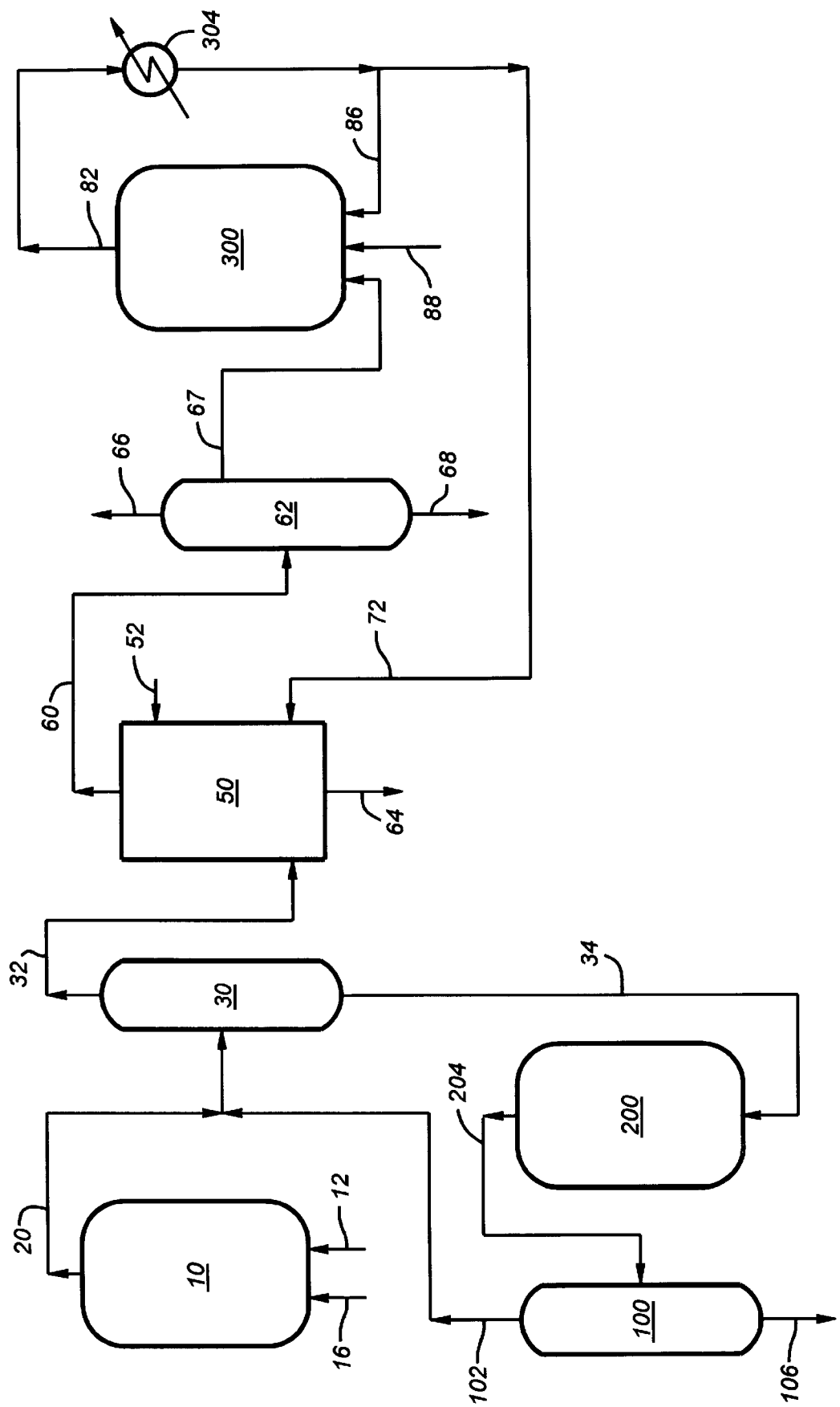
FIG. 1 is a schematic flow sheet with conventional parts omitted showing the general reaction and recovery sequence of the present invention for the manufacture and purification of methyl tertiary butyl ether.

Turning now to FIG. 1, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reaction zone 10 containing a bed of a solid etherification catalyst, such as a solid resin etherification catalyst (e.g., a strongly acidic ion exchange resin of the type disclosed above, such as "Dowex 50", "Nalcite HCR" and "Amberlyst 15").

A substantially peroxide-free tertiary butyl alcohol feedstock is continuously charged to the etherification reaction zone 10 by a line 12. Methanol is charged to the etherification reaction zone 10 by a line 16.

In order to achieve maximum selectivity to MTBE, and optimum conversion per pass, an excess of methanol in the liquid feed is desirable. Thus, the molar ratio of methanol to t-butanol should be between 10:1 and 1:10 if the yield of desired MTBE is to be maximized. The preferred methanol-to-tertiary butanol molar ratio is from 1:1 to 5:1. More preferably, the feed mixture contains a molar ratio of about 1.1 to about 3 moles of methanol per mol of tertiary butyl alcohol. e.g. 2:1. The feed may contain minor amounts of other components including water, alcohols such as isopropanol, ketones such as acetone, peroxides and hydroperoxides such as di-t-butyl peroxide and allyl t-butyl peroxide, as well as esters such as t-butyl formate. Preferably, bee feed mixture will be substantially completely free from peroxide contaminants.

Typically, MTBE is generated continuously in up to ca. 30 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated using the equation:

$$\frac{(\text{Wt \% Conc. of } tBA \text{ in Feed} - \text{Wt \% Conc. of } tBA \text{ in Product})}{\text{Wt \% Conc. of } tBA \text{ in Feed}} \times 100$$

Selectivities for methyl t-butyl ether (MTBE, mole %) and isobutylene ($C_4H_8$, mole %) are estimated from:

$$\frac{\text{Moles of } MTBE(\text{or } C_4H_8) \text{ in Product}}{\text{moles of } tBA \text{ converted}} \times 100$$

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., a still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is within the ratio of about 2.0 moles of methanol per mole of tertiary butyl alcohol, and the reaction is conducted at a temperature of about 100° C. at a feed rate of about 2.0 volumes of feed mixture per volume of catalyst per hour, a representative etherification reaction product will have the composition in part shown by the following table:

ETHERIFICATION REACTION PRODUCT

| Component | wt. % |
| --- | --- |
| Water | 14.0 |
| Methanol | 27.6 |
| Isobutylene | 3.0 |
| TBA[1] | 14.1 |
| MTBE[2] | 34.5 |
| Other[3] | 6.8 |

[1] Tertiary butyl alcohol
[2] Methyl tertiary butyl ether
[3] Includes the acetone, propanol, ditertiary butyl peroxide, tertiary butyl formate, etc., initially present in the tertiary butyl alcohol feedstock and DME (formed from methanol).

The effluent from the primary reactor is fed to the methyl tertiary butyl ether recovery distillation tower which recovers MTBE, isobutylene and some methanol overhead while water, tBA and methanol are removed in the bottoms. The bottoms from the primary fractionator, comprising water, t-butanol, methanol and isopropanol, are fed into a second etherification unit and reacted over the acidic fluoride-treated Y-zeolites for additional cogeneration of isobutylene and MTBE.

Thus, the etherification reaction product charged to the first MTBE distillation zone 30 by way of the charge line 20 is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reactor 10 is taken overhead from the first distillation zone 30 by a line 32 and such that substantially all of the tertiary butyl alcohol exits the column 30 through the line 34. As a consequence, the first distillation fraction 32 taken overhead from the distillation zone 30 will comprise substantially all of the isobutylene, methyl tertiary butyl ether and some of the methanol and water charged to the first distillation zone 30. The first heavier distillation fraction 34 discharged from the first distillation zone 30 will comprise methanol, tertiary butyl alcohol and water, and will normally contain from about 30 to about 40 wt. % of methanol, from about 20 to about 30 wt. % of tertiary butyl alcohol, from about 35 to about 20 wt. % of water; oxygen-containing impurities comprising the balance.

The first heavier distillation fraction 34 is charged to second stage reaction zone 200 containing a bed of a strongly acidic fluoride-containing Y-zeolite having a silica:alumina ratio of 100:1 to 10:1 and a unit cell size of from 24.20 to 24.45 or a fluoride-modified silicoaluminophosphate (SAPO).

Within the second stage reaction zone 200 the feed is brought into contact with the catalyst under reaction conditions including a pressure of about 50 to about 500 psia, and more preferably from about 200 to about 300 psia, a temperature of about 120° to about 250° C., and more preferably from about 80° to about 140° C., and still more preferably from about 180° to about 220° C. Contact time within the second stage etherification reaction zone is suitably such that about 0.5 to about 20 volumes of feed per volume of etherification catalyst per hour are fed to the second stage etherification reaction zone 200 and, more preferably from about 1 to about 4 volumes of feed per volume of etherification catalyst per hour. As a consequence, the tertiary butyl alcohol in the first heavier distillation fraction is converted primarily to isobutylene, although a minor amount of methyl tertiary butyl ether is formed by reaction of the isobutylene with methanol present in the first heavier distillation fraction.

In certain circumstances, it may be particularly desirable that the tBA conversion be high enough (e.g., 80% or greater), such that the crude product mix phase separates into an isobutylene-MTBE product-rich phase and a heavier aqueous methanol phase. Preferably such a product phase separation would be achieved at as low an etherification temperature as possible, but particularly in the range 160°–240° C.

In accordance with the present invention the second stage reaction product is discharged from the second stage methyl tertiary butyl ether etherification reaction zone 200 by a line 202 leading to a second distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a second lighter distillation fraction comprising isobutylene, methyl tertiary butyl ether, tertiary butyl alcohol and methanol that is discharged by a line 102 and a second heavier distillation fraction comprising water, which is discharged by a line 106.

In accordance with the present invention the second light distillation fraction 102 is recycled to the line 20 leading to first MTBE distillation zone 30.

The first lighter distillation fraction 32 and a recycle fraction 72 are charged to a solvent extraction tower 50. As explained in greater detail hereafter, the recycle fraction 72 contains methyl tertiary butyl ether, methanol and isobutylene. Within the solvent extraction tower 50 the hydrocarbon streams 32 and 72 are counter-currently contacted with water introduced by a water charge line 52 so that methanol can be extracted from the other hydrocarbons with water to thereby form an aqueous raffinate phase and a hydrocarbon extract phase. The efficiency of the extraction is improved by the isobutylene present in the extraction tower.

Within the methanol extraction tower 50, solvent extraction conditions are established for countercurrent solvent extraction including a ratio of hydrocarbon feed to water within the range of about 0.8 to 1.8 volumes of hydrocarbon per volume of water per hour, and more preferably, a ratio of about 1.0 to about 1.5 volumes of hydrocarbon per volume of water. Extraction conditions to be established may suitably include a temperature of about 20° to about 60° C., and more preferably, from about 30° to about 40° C., and a pressure of about 50 to 500 psia, and more preferably from about 50 to 150 psia.

As a consequence, a supernatant extract will be formed which is withdrawn from the top of the methanol solvent extraction tower 50 by line 60 leading to a second methyl tertiary butyl ether purification distillation column 62. The raffinate is discharged from the solvent extraction tower 50 by way of a bottoms charge line 64.

The extract is charged to a third distillation column 62, where distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a third lower boiling (lighter) isobutylene distillation fraction 66, an intermediate water fraction 67 and a higher boiling (heavier) second distillation fraction 68 consisting essentially of product, namely methyl tertiary butyl ether.

The third intermediate boiling distillation fraction 67 will comprise isobutylene and is reacted with methanol in a secondary isobutylene finishing reactor 300 to form additional methyl tertiary butyl ether. The reaction of isobutylene with methanol is exothermic and it is necessary to provide for positive control of the reaction temperature. This is accomplished by limiting the rate at which isobutylene is charged to the secondary isobutylene reactor and by diluting the charged isobutylene with a stream of cooled recycled reaction product.

Thus, the isobutylene in line 67 is charged through line to the secondary isobutylene reactor 300 together with methanol charged by the line 88. The methanol should be charged by the line 88 in an amount sufficient to provide for a molar ratio of about 0.3 to about 0.8 mole of methanol per mol of isobutylene. The secondary reactor 300 may suitably contain a fixed bed of an isobutylene/methanol etherification catalyst, such as a bed of Amberlyst 15 sulfonated polystyrene-divinyl benzene copolymer acidic ion exchange resin.

Etherification reaction conditions established in the secondary reaction zone 300 may include, for example, a temperature of about 35° to about 100° C., a pressure of about 150 to 250 psia, and a flow rate of about 0.5 to 10 volumes of feed per volume of solid resin etherification catalyst per hour. As a consequence, the methanol and a portion of the isobutylene contained in the feed will be converted to methyl tertiary butyl ether.

An isobutylene conversion product 82 discharged from the secondary reactor 300 passes through heat exchanger 304 where the reaction product is cooled to a temperature of about 30° to about 100° C. About 10 to 20 mol % of the reaction product is recycled by the line 72 to the methanol extraction tower. The remainder of the reaction product is recycled to the secondary reactor by the line 86 as a diluent.

Figure 2:
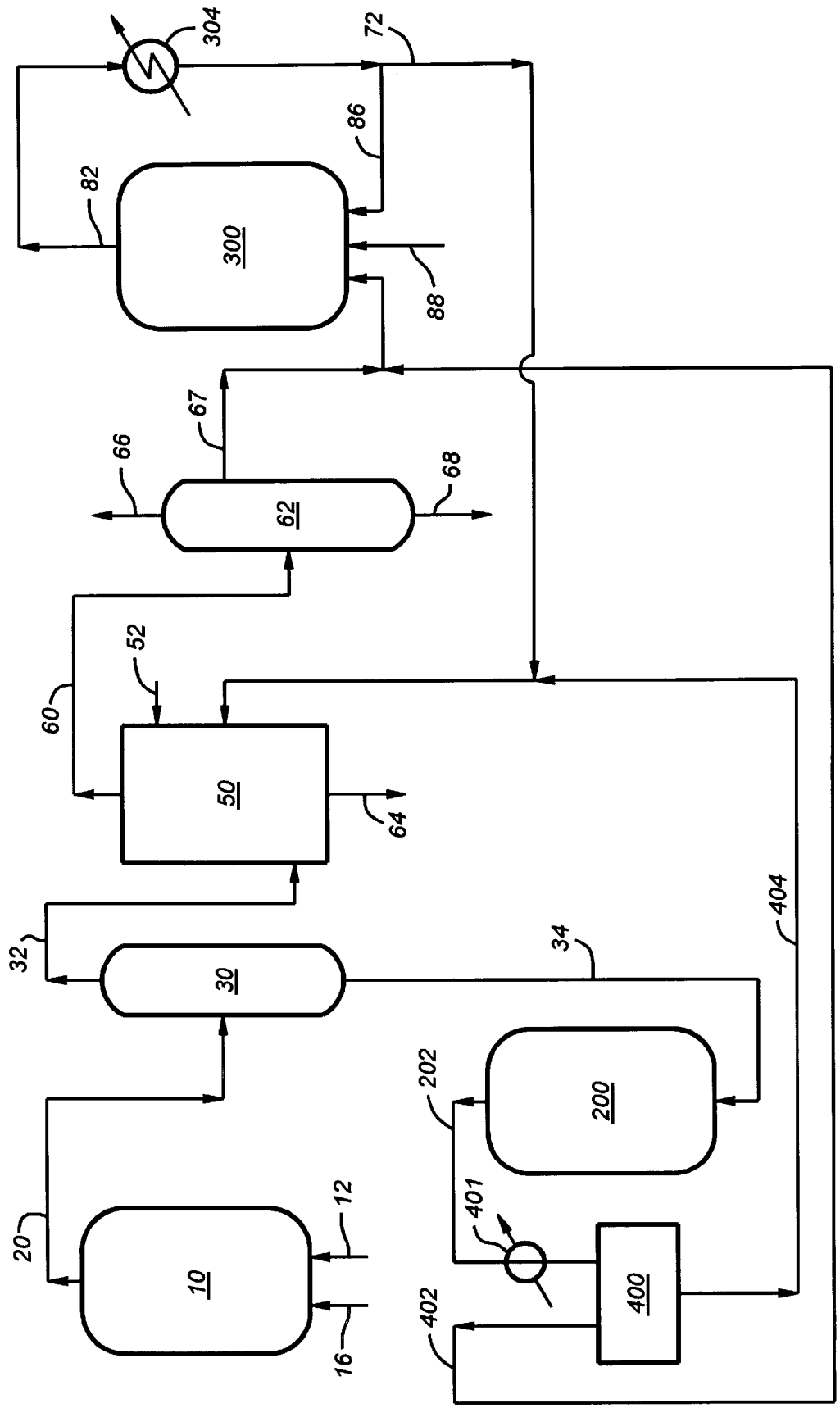
FIG. 2 is a schematic flow sheet with conventional parts omitted showing the general reaction and recovery sequence of the present invention for the manufacture and purification of methyl tertiary butyl ether.

Turning next to FIG. 2, there is shown a schematic flow sheet illustrating another preferred method for the practice of the present invention.

The general reaction sequence of this embodiment of the present invention differs from the embodiment shown in FIG. 1 in the different treatment of the second stage reaction product. In accordance with this embodiment, a primary etherification reaction zone 10 containing a bed of a solid etherification catalyst is provided, as described above in respect of FIG. 1. Thus, a tertiary butyl alcohol feedstock is continuously charged to the etherification reaction zone 10 by a line 12. Methanol is charged to the etherification reaction zone 10 by a line 16.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

The etherification reaction product charged to the first MTBE distillation zone 30 by way of the charge line 20 is fractionated therein under distillation conditions, as described above, so that substantially all of the MTBE in the etherification reaction product 20 is taken overhead from the first distillation zone 30 by a line 32 and such that substantially all of the tertiary butyl alcohol exits the column 30 through the line 34. The first distillation fraction 32 taken overhead from the distillation zone 30 will comprise substantially all of the isobutylene, methyl tertiary butyl ether and some of the methanol and water charged to the first distillation zone 30. The first heavier distillation fraction 34 discharged from the first distillation zone 30 will comprise methanol, tertiary butyl alcohol and water.

In accordance with this embodiment of the present invention, the tBA conversion will be 80% or greater so that the crude product mix phase separates into a lighter isobutylene-MTBE product-rich phase and a heavier aqueous methanol phase. This is accomplished by conducting the reaction at as low a low reaction temperature in the range 160°–240° C.

Within the second stage reaction zone 200 the feed is brought into contact with the catalyst under reaction conditions including a pressure of about 50 to about 500 psia, and more preferably from about 200 to about 300 psia, a temperature of about 160° to about 240° C. Contact time within the second stage etherification reaction zone is suitably such that about 0.5 to about 20 volumes of feed per volume of etherification catalyst per hour are fed to the second stage etherification reaction zone 200 and, more preferably from bout 1 to about 4 volumes of feed per volume of etherification catalyst per hour. As a consequence, at least about 80% of the tertiary butyl alcohol in the first heavier distillation fraction is converted to a second reaction product composed primarily of isobutylene, although a minor amount of methyl tertiary butyl ether is formed.

The second reaction product comprising methanol, unreacted tertiary butyl alcohol, isobutylene, methyl tertiary butyl ether and water is discharged from the second reactor 200 by a line 202 leading to heat exchanger 401 where the reaction product is cooled to a temperature of about 80° to about 120° F. (preferably 100° F.) at a pressure of about 120 to about 150 psig. The cooled reaction product is charged to a drum 400 where phase separation occurs. A lighter phase comprising isobutylene, methyl tertiary butyl ether and tertiary butyl alcohol is discharged from the drum 400 by a line 402 and the heavier aqueous fraction comprising water and methanol is discharged from the drum 400 by a line 404.

The first lighter distillation fraction 32 and a recycle fraction 72 are charged to a solvent extraction tower 50. In accordance with this embodiment of the present invention, the heavier methanol/water fraction 404 from the separation drum 400 is charged to the solvent extraction tower 50 together with the recycle fraction 72. Within the solvent extraction tower 50 the hydrocarbon streams 32 and 72 are counter-currently contacted with water introduced by a water charge line 52 so that methanol can be extracted from the other hydrocarbons with water to thereby form an aqueous raffinate phase and a hydrocarbon extract phase.

Within the methanol extraction tower 50, solvent extraction conditions are established for countercurrent solvent extraction, as explained above in respect of FIG. 1 to form a supernatant extract that is withdrawn from the top of the methanol solvent extraction tower 50 by line 60 leading to a third methyl tertiary butyl ether purification distillation zone 62. The raffinate is discharged from the solvent extraction tower 50 by way of a bottoms charge line 64.

The extract is charged to a third distillation zone 62, where distillation conditions are established, as explained above, so as to thereby form a third lower boiling (lighter) water distillation fraction 66, an intermediate isobutylene fraction 67 and a higher boiling (heavier) second distillation fraction 68 consisting essentially of methyl tertiary butyl ether.

The third intermediate boiling isobutylene distillation fraction 67 and the lighter fraction 402 from the separation drum 400 are reacted with methanol in a secondary isobutylene finishing reactor 300 to form additional methyl tertiary butyl ether. An isobutylene conversion product 82 discharged from the secondary reactor 300 passes through heat exchanger 304 where the reaction product is cooled to a temperature of about 30° to about 100° C. About 10 to 20 mol % of the reaction product is recycled by the line 72 to the methanol extraction tower. The remainder of the reaction product is recycled to the secondary reactor by the line 86 as a diluent.

DESCRIPTION OF THE CATALYSTS OF THE PRESENT INVENTION

In accordance with one embodiment of the present invention, an acidic, fluoride-treated Y-zeolite catalyst is used in a second step to convert the t-butanol to isobutylene and methyl tertiary butyl ether. The instant catalyst composition provides for etherification of the bottoms from the primary fractionator comprising crude t-butanol/methanol feedstock at a temperature in excess of 120° C., e.g. 140°–240° C., to complete the conversion of the remaining TBA fraction to MTBE plus isobutylene. The t-butanol/methanol feedstock comprises four principal components, viz-water, t-butanol, methanol and isopropanol. The preferred fluoride-treated Y-zeolites achieve >90% conversion, are stable at high temperatures, and exhibit greater than 2000 hours of service.

The exchange of the sodium ions of the Y-zeolite by rare earth ions has been reviewed (see, for example, R. Rudham and A. Stockwell, The Chemical Society Specialist Periodical Report—Catalysis, Vol. I, 1977, Chapter 3). The preferred acidic Y-zeolites for the practice of this invention have silica:alumina ratios in the range 100:1 to 10:1. A suitable range is 100:1 to 5:1. The preferred range is 50:1 to 7:1.

Particularly effective in the subject synthesis of MTBE are the synthetic Y-zeolites. Preferably said zeolites should be in a strongly acidic form whereby some, or all, of the cations (Group I or II, alkali or alkaline earth metal ions such as sodium, potassium, calcium or magnesium) are exchanged by protons either through ammonium exchange followed by thermal stabilization (deammoniation, removal of $NH_3$) at elevated temperatures (e.g. 400°–500° C.) through mineral acid treatment, etc. Alternatively, said Y-zeolites may be rare-earth exchanged with, for example, a mixture of rare-earth salts, by treatment with lanthanum salts, etc. Said rare-earth exchanged Y-zeolites would then have a Si:Al ratio of 1.5 to 3.

Good results are obtained using a catalyst that comprises an acidic, fluoride-treated Y-zeolites, particularly catalysts containing the isostructural group of faujasite zeolites that include the synthetic Y-zeolites. The preferred Y-zeolites are the ammonium exchanged and rare earth exchanged Y-zeolites.

The unit cells of zeolites X and Y are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

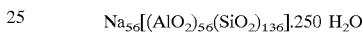

$Na_{56}[(AlO_2)_{56}(SiO_2)_{136}] \cdot 250\ H_2O$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48 giving a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

The unit cell size for the instant catalyst may be 24.20 to 24.45.

Illustrative of suitable Y-zeolites for the practice of this invention include Linde SK-500, a rare-earth exchanged Y-zeolite, having a Si:Al ratio of 1.5→2.5, PQ Corporation's CP 304-37, a thermally-stabilized, ammonium-exchanged Y-zeolite having a silica:alumina ratio of ca. 11:1, with a silica-alumina binder, as well as CP 316-26, another ammonium exchanged Y-zeolite, this time having a silica-to-alumina ratio of 46, LZY-82 from UOP having a silica:alumina ratio of 7.8 and a unit cell size of 24.53 Å, and LZY-85 having a silica:alumina ratio of 9.1 and a unit cell size of 24.49 Å.

SILICOALUMINOPHOSPHATES

Silicoaluminophosphate (SAPO) molecular sieves are also useful in the instant invention. The SAPOs have the general formula:

$$nR.(Si_x Al_y P_z)O_2.bH_2O$$

where R=an organic compound and x+y+z=1.

Silicoaluminophosphate molecular sieves useful in the practice of the process of the present invention include SAPO-5, SAPO-37, SAPO-11 and SAPO-31.

Because it has the faujasite structure topology, SAPO-37 is a material of particular industrial interest. U.S. Pat. No. 4,681,864 (Edwards et al.) disclosed a catalytic cracking catalyst composition comprising the SAPO-37 molecular sieve component. Derouane et al. disclosed in U.S. Pat. No. 4,898,722 an improved method for synthesis of improved SAPO-37 using a two-phase reaction mixture. The activity of SAPO-37 is improved when its precursor (containing organic template) is calcined in nitrogen to avoid deterioration of the framework by water.

SAPO-5 is another large-pore SAPO material having potential for acid-catalyzed reactions. EP 202,325, and also WO 86/03138 reported the composition of cracking catalysts containing SAPO-5. Medium-pore SAPO molecular sieves including SAPO-11 and SAPO-31 have recently attracted significant interest. U.S. Pat. No. 4,689,138 reported an isomerization-dewaxing process using SAPO-11 and SAPO-41.

SAPO-5, SAPO-37, SAPO-11 and SAPO-31 are all suitable for the generation of MTBE. Since they are classified as mildly acidic, the SAPO materials provide good selectivity to ethers and generate less undesirable di-isobutylene at elevated temperatures.

It has been discovered that acidic fluoride-treated Y-zeolites, and SAPOs, have a number of improved properties for the production of MTBE. Most importantly they possess the stability at high temperatures necessary for a second stage process of the type described herein.

The acid useful for modifying the zeolites is selected from the group consisting of fluoride-containing compounds such as ammonium fluoride or silicon hexafluoride compounds, hydrogen fluoride, hydrofluoric acid, or fluorosulfonic acid and its congeners such as fluorosulfonic acid, trifluoromethane sulfonic acid (triflic acid), as well as triflic anhydride. These fluorosulfonic acids can be substituted with a variety of alkyl groups, as in the case of trifluoromethanesulfonic acid. Methods of preparing these triflic acid-modified catalysts are illustrated in the accompanying Example 2 and 3.

The fluoride-modified zeolites are prepared by treating the Y-zeolite or dealuminized Y-zeolite with hydrogen fluoride, with an aqueous solution of hydrofluoric acid, with ammonium fluoride, or with a solution of HF or $NH_4F$ in a suitable aliphatic hydrocarbon solvent. Preferably the hydrogen fluoride is added to said zeolite as a solution of hydrofluoric acid in distilled water. The method of preparing these HF-modified catalysts is illustrated in the accompanying Examples 1 and 5.

For example, the treatment of the Y-zeolites with fluoride ion is accomplished by adding a solution of from 1% to about 60% or 0.1N to 10N fluoride compound such as, for example, hydrogen fluoride, ammonium fluoride, triflic acid, fluorosulfonic acid or triflic anhydride in distilled water to 100 g of a Y-zeolite or dealuminated Y-zeolite, stirring from 1 hour to at least 24 hours, under nitrogen, filtering and washing the solids with distilled water, then drying in vacuo at 40° C. overnight plus 150° C. for 4 hours.

Said catalysts should have a residual acidity in the range 0.1 to 100 mg KOH/g and they may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

The examples which follow illustrate the second stage synthesis of MTBE and isobutylene from crude t-butanol/methanol feedstocks using the acidic, fluoride-treated Y-type zeolites, particularly in the form of extrudates. The examples are only intended as a means of illustration and it is understood the invention is not meant to be limited thereby.

EXAMPLE 1 (6798-6R)

This example illustrates the preparation of a hydrogen fluoride-modified Y-zeolite.

To 100 g of Y-zeolite (CP316-26, an ammonium-exchanged, thermally-stabilized Y-zeolite having a silica:alumina ratio of 46 and a unit cell size of 24:26 Å, in 1/16" diameter extruded form) was added a (3.8N) solution of 48% hydrofluoric acid (50 g) in distilled water (100 g). The mixture was stirred overnight, under nitrogen, filtered and the solids washed with distilled water, then dried in vacuo at 40° C., overnight, plus 150° C. for 4 hours.

The recovered white extrudates were found to comprise on analysis:

Fluoride, 1.6%
Water, 1.2%
Acidity, 20.2 mg KOH/g

EXAMPLE 2 (6798-5)

This example illustrates the preparation of a triflic acid-modified Y-zeolite.

To 100 g of Y-zeolite (CP316-26 that had been dried in vacuo at 175° C. for 3 hours and had a water content of 0.54%) was added a solution (0.67N) of trifluoromethane sulfonic acid (40 g) in dried acetone (400 cc, dried over 4 Å sieve). The mixture was stirred overnight under nitrogen, filtered and the solids washed with dried acetone then dried in vacuo at 40° C. overnight, plus at 150° C. for 4 hours.

The recovered reddish-brown extrudates were found to comprise by analysis:

Fluoride, 1.6%
Water, 0.54%
Acidity, 29.7 mg KOH/g

EXAMPLE 3 (6798-3R)

This example illustrates the preparation of a triflic acid-modified Y-zeolite.

To 100 g of rare-earth exchanged Y-zeolite (Linde SK-500, having a silica:alumina ratio of 2.9, in 1/16" diameter extruded form that had been dried in vacuo at 175° C. for 3 hours and had a water content of 0.58%) was added a solution of (0.67N) trifluoromethanesulfonic acid (40 g) in dried acetone (400 cc, dried over 4 Å sieve). The mixture was stirred overnight under nitrogen, filtered and the solids washed with dried acetone then dried in vacuo at 40° C., overnight, plus at 150° C. for 4 hours.

The recovered brown extrudates were found to comprise by analysis:

Water, 0.89%

Acidity, 52.6 mg KOH/g

EXAMPLE 4

Example 4 with Code No. 2143CT90 was prepared by ion exchange of the Y-82 zeolite/alumina extrudates from UOP with 2.5 wt % aqueous ammonium fluoride solution at 60° C. for 4 hours and calcined at 593° C. for 3 hours.

EXAMPLE 5

Example 5 with Code No. 6798-6 illustrates the preparation of a hydrofluoric acid-treated Y-zeolite (6.4N).

To 500 cc of sample of CP316-26 zeolite/alumina extrudates from PQ Corp. was added a 10 vol % HF in distilled water in sufficient quantity to cover the extrudates. The mix was allowed to stand for 1 hour, excess water removed by rotary evaporation and the residual solids dried at 200° C., overnight.

EXAMPLE 6

This example illustrates the cosynthesis of isobutylene and MTBE from a crude aqueous t-butanol/methanol feedstock using the ammonium fluoride-modified Y-82 zeolite (Example 4).

The etherification reaction was conducted in a tubular reactor (½" id, 12" long) constructed of 316 stainless steel, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 50 cc of ammonium fluoride-treated Y-zeolite extrudates (Example 4). A screen of glass wool was placed at the top and bottom of the reactor to ensure the catalyst would remain in the middle portion.

The catalyst bed was treated with a crude t-butanol/methanol feed mix also containing sizeable quantities of water and isopropanol components, upflow, at a feed rate of 50 cc/hour, while the reactor was held at 140° C. with a total pressure of 300 psi. Samples of effluent were collected periodically on stream and analyzed by glc and gc-ir.

Typical analyses data for samples taken under these conditions are summarized in Table V. Performance at higher temperatures (160°, 180°, 200° C.) was determined using the same procedures. These results are also given in Table V.

Operating at 200° C., where the effluent comprises two phases, the t-butanol conversion level and isobutylene/MTBE selectivities are as follows:

t-Butanol conversion=93%

Isobutylene selectivity=90 mole %

MTBE selectivity=7 mole %

Conclusion

Our results demonstrate that a two-stage etherification process employing the catalysts of this invention, such as are demonstrated in Examples 4 and 5, in the second-stage reactor permits high conversion of t-butanol at temperatures of 120°–200° C. The catalyst also demonstrates a good lifetime activity and hydrothermal stability at high temperature.

TABLE I

Catalytic Activities of Zeolite Samples for MTBE Synthesis at 200° C.

| Sample Code No. (200° C.) | Catalyst Description | tBA Conv. (%) | Molar Select. (%) C₄H₈ | MTBE |
|---|---|---|---|---|
| 2143-CT-90 | NH₄F/Y-82 | 93 | 90 | 10 |
| 2141-CT-90 | NH₄F/Y-82 | 93 | 91 | 9 |
| 6798-6 | HF/CP316-26 | 94 | 90 | 7 |
| 6798-3 | TF/SK-500 | 91 | 87 | 13 |
| 6798-5 | TF/CP316-26 | 94 | 94 | 6 |

TABLE II

Catalytic Activities of Zeolite Samples for MTBE Synthesis at 160° C.

| Sample Code No. (160° C.) | Catalyst Description | tBA Conv. (%) | Molar Select. (%) C₄H₈ | MTBE |
|---|---|---|---|---|
| 2143-CT-90 | NH₄F/Y-82 | 64.6 | 34 | 66 |
| 2142-CT-90 | NH₄F/Y-82 | 45.8 | 41 | 59 |
| 2141-CT-90 | NH₄F/Y-82 | 66.9 | 35 | 65 |
| 6798-6 | HF/CP316-26 | 63.0 | 36 | 64 |
| 6798-3 | TF/SK-500 | 59.8 | 36 | 64 |
| 6798-4-1R | HF/SK-500 | 53.8 | 36 | 64 |
| 6798-5 | TF/CP316-26 | 63.7 | 40 | 60 |
| 6798-7 | HF/CP304-37 | 59.4 | 37 | 63 |
| 2140-CT-90 | NH₄F/Y-85 | 60.0 | 36 | 64 |
| 6798-41 | TA/SK-500 | 60.0 | 37 | 63 |

TABLE III

Performance of Ammonium Fluoride-treated Catalyst (Example 1, 2143-CT-90)

| Sample Code No. | Time On Stream (days) | Operating Temp. (°C.) | tBA Conv. (%) | Molar Select. (%) C₄H₈ | MTBE |
|---|---|---|---|---|---|
| 6945-23-2R | 2 | 200 | 93 | 89 | 8.7 |
| 6945-23-6 | 17 | 200 | 89 | 81 | 14 |
| 6945-23-14 | 52 | 220 | 92 | >99 | 12 |
| 6945-23-18 | 81 | 220 | 82 | 96 | 24 |

TABLE IV

Performance of Hydrofluoric Acid-treated CP316-26 Catalyst (Example 2, 6798-6R)

| Sample Code No. | Time On Stream (days) | Operating Temp. (°C.) | TBA Conv. (%) | Molar Select. (%) C₄H₈ | MTBE |
|---|---|---|---|---|---|
| 6945-67-1 | 1 | 200 | 93 | 59 | 7.2 |
| 6945-67-4 | 19 | 220 | 82 | 95 | 18 |
| 6945-67-9 | 53 | 220 | 80 | 89 | 23 |
| 6945-67-14 | 85 | 220 | 80 | 84 | 16 |

Catalyst Screening Studies

A total of ten fluoride-treated zeolites have been evaluated in the subject process. These include Y-zeolites such as:

LZY-82, LZY-85, CP 316-26, CP 304-37 and SK-500 treated with:

Ammonium fluoride, HF, triflic acid and triflic anhydride.

The feedstock used in this evaluation has the approximate composition of 25.8% water, 36.9% methanol, 10.6% 2-propanol and 26.0% t-butanol. This feedstock simulates the composition of the bottoms from the primary fractionator, downstream of the first stage etherification reactor.

In the first study, a sample of ammonium fluoride-treated Y-82 zeolite, gave tBA conversions at 180° C. and 200° C., as measured by GLC, of 88% (sample 6834-64-6) and 93% (sample 6834-64-7, see Table V), respectively. At both temperatures, the effluent product appeared as two phases—a lighter isobutylene/MTBE product phase and a heavier aqueous alkanol phase. In this experimental series, a sight glass was used to measure the relative sizes of these phases so that isobutylene and MTBE molar selectivities could be accurately calculated. Gas chromatograph-mass spec. analyses of Sample 6834-64-3 indicated the formation of small quantities of diisobutylene and isopropyl t-butyl ether (IPTBE).

Two other ammonium fluoride-treated Y-zeolites have also been screened in a similar manner (see Tables VI and VII). Sample 2042-CT-90 appeared to deactivate at the higher screening temperatures (180°–200° C.), see Table VI), t-butanol conversions were <30% and there was no product phase separation. A repeat run gave similar results. Sample 2141-CT-90 performed like the first sample of $NH_4F$ modified Y-82 (cf. Tables V and VII). Two phase effluent products were observed at both 180° and 200° C. and for sample 6834-75-R4 the calculated tBA conversion was 93% and the isobutylene/MTBE molar selectivities 95 and 9.1%, respectively.

Five fluoride-treated Y-zeolites were then tested in the same service. These solid acids included:

a) HF-treated CP316-26, 1/16"E (Sample 6798-6, Run 6834-81, see Table VIII).

b) TF-treated SK-500, 1/16"E (Sample 6798-3, Run 6834-84, see Table IX).

c) HF-treated SK-500, 1/16"E (Sample 6798-4, Run 6834-93, see Table X).

d) TF-treated CP316-26, 1/16"E (Sample 6798-5, Run 6834-96, see Table XI).

e) HF-treated CP304, 1/16"E (Sample 6798-7, Run 6945-11, see Table XII).

The HF/CP316-26 gave excellent performance—94% tBA. Conversion per pass at 200° C. (sample 6834-81-R4) with 91% isobutylene selectivity and 7.2% MTBE. Similarly the triflic acid (TF)-modified SK-500 gave 91% tBA conversion at 200° C./sample 6834-84-R4). The DME and diisobutylene concentrations in these samples are typically <400 ppm for Sample 6834-84-R4 and the isopropyl t-butyl ether (IPTBE) content is 0.2%. The triflic acid-treated dealuminized Y from PQ (Sample 6798-5) also gave 94% tBA conversion at 200° C. operating temperatures.

Other solid acids evaluated for this purpose include another ammonium fluoride-modified Y-85 and a triflic anhydride (TA) treated SK-500. The results of these runs are given in Tables XIII and XIV.

A summary of the performances of the five best candidates (giving >90% TBA conversion at 200° C.) and the performance of ten catalyst samples at 160° C. are given in Table I and II.

TABLE V

Recycle Stream Studies
$NH_4F/Y-82$ (2143-CT-90)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE |
| 683444 | 2143-CT-90[a] | 50 | | | FS-1[b] | 26.5 | 36.0 | 11.6 | 26.0 | | | | |
| | | | 140 | 1 | 1 | 30.3 | 32.1 | 11.5 | 2.1 | 11.9 | 11.9 | | |
| | | | | | →2 | 30.1 | 31.9 | 11.5 | 22 | 11.7 | 12.5 | | |
| | | | 160 | 2 | 3[c] | 32.4 | 34.2[d] | 11.8[d] | 3.1 | 9.2[d] | 9.2[d] | | |
| | | | | | 4[c] | 32.5 | 34.2 | 11.9 | 3.1 | 9.2 | 9.2 | | |
| | | | 180 | 3 | f5 | 38.8[e] | 39.7[d] | 11.9[d] | 2.6 | 3.4[d] | 3.5[d] | 0.1[d] | 0.1[d] |
| | | | | | f6 | 38.5 | 40.1 | 11.9 | 2.8 | 3.2 | 3.5 | 0.1 | ? |
| | | | 180 | R-1 | g,iR-2 | 18.6 | 23.1 | 9.8 | 31.0 | 4.6 | 12.8 | | 0.1 |
| | | | | | | 36.3 | 36.5 | 12.2 | 4.6 | 5.0 | 5.3 | | 0.1 |
| | | | 200 | 4 | 7 | 39.3[c] | 41.8 | 12.4 | 3.0 | 1.9 | 1.5 | | |
| | | | | | f8 | 38.3[e] | 42.1 | 12.7 | 3.1 | 2.2 | 1.6 | | |
| | | | 200 | R-2 | g,j→R4 | 12.2 | 16.0 | 7.1 | 57.4 | 1.4 | 5.8 | | 0.2 |
| | | | | | h | 38.2 | 42.2 | 13.4 | 2.5 | 1.9 | 1.7 | | |

[a]UOP's Y-82 zeolite, $NH_4F$ treated, 6 hr, 1/16" E
[b]Recycle stream composition from YES
[c]Sample shows onset of phase separation
[d]Confirmed by gc-ms, plus: t-Butyl isopropyl ether, 2,4,4-triethyl-1-pentene and 2,4,4-trimethyl-1-pentene
[e]Insufficient sample for analyses
[f]Similar analyses for repeat sample
[g]Repeat run, collected over 3 hrs., sampled from sight glass
[h]Recovered catalyst: $H_2O$, 0.43%; Acidity, 0.036 meq/g
[i]Relative size of phases, 1:5.8 (t/b)
[j]Relative sizes of phases, 1:35 (t/b)

TABLE VI

Recycle Stream Studies
NH$_4$F/Y-82 (2143-CT-90)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE |
| 6834-67 | 2042-CT-90[a] | 50 | | | FS-1[b] | 26.4 | 36.1 | 11.6 | | 26.0 | | | |
| | | | 140 | 1 | 1 | 28.7 | 33.3 | 11.6 | 1.3 | 21.5 | 3.3 | | 0.1 |
| | | | | | 2 | 28.4 | 34.6 | 11.6 | 1.8 | 19.3 | 4.3 | | |
| | | | 160 | 2 | 3 | 30.4 | 32.3 | 11.5 | 3.3 | 14.1 | 8.1 | | 0.2 |
| | | | | | 4 | 30.7 | 32.5 | 11.4 | 2.8 | 17.1 | 5.5 | | 0.1 |
| | | | 180 | 3 | 5 | 28.6 | 34.3 | 11.3 | 1.0 | 23.1 | | | |
| | | | | | [c]6 | 28.3 | 34.6 | 11.5 | 23.7 | 1.1 | | | |
| | | | | R-1 | [c]R-2 | 27.1 | 35.3 | 11.7 | 0.4 | 25.2 | 0.3 | | |
| | | | 200 | 4 | 7 | 29.6 | 34.1 | 11.5 | 2.5 | 20.1 | 2.2 | | 0.1 |
| | | | | | [c]8 | 29.4 | 34.3 | 11.4 | 2.0 | 21.1 | 1.8 | | 0.1 |
| | | | | R-2 | [c]R-4[d] | 28.2 | 34.7 | 11.7 | 1.3 | 23.1 | 0.9 | | |

[a]UOP's Y-85 zeolite, NH$_4$F treated, 6 hr, 1/16" E
[b]Recycle feed composition from YES
[c]Repeat run, collected over 3 hrs, sampled from sight glass
[d]Recovered catalyst: H$_2$O, 3.0%, Acidity, 0.03 meq/g
[e]Similar analyses for repeat sample

TABLE VII

Recycle Stream Studies
NH$_4$F/Y-82 (2143-CT-90)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE |
| 6834-75 | 2141-CT-90[a] | 50 | | | FS-1[b] | 26.0 | 35.9 | 11.7 | | 26.4 | | | |
| | | | 140 | 1 | 1 | 31.0 | 31.3 | 11.3 | 2.3 | 11.2 | 12.7 | 0.4 | 0.2 |
| | | | | | 2 | 30.9 | 31.2 | 11.5 | 2.3 | 11.0 | 12.8 | 0.4 | 0.2 |
| | | | 160 | 2 | 3 | 33.0 | 33.2 | 11.7 | 3.3 | 9.0 | 9.8 | 2.2 | 0.2 |
| | | | | | 4 | 32.0 | 31.2 | 11.1 | 3.0 | 12.6 | 10.0 | 2.2 | 0.2 |
| | | | 180 | 43 | 5 | 2.2 | 8.5 | 9.1 | 58.1 | 2.5 | 17.2 | | |
| | | | | | | 41.2 | 38.2 | 11.6 | 2.7 | 3.0 | 3.3 | 0.2 | |
| | | | | | [h]6 | [d]39.4 | 39.4 | 11.8 | 2.8 | 3.1 | 3.6 | | |
| | | | | R-1 | [e,f]R-2 | 4.5 | 9.7 | 6.2 | 53.8[i] | 5.6[i] | 17.7[i] | 0.5 | 0.5 |
| | | | | | | 36.0 | 36.4 | 12.1 | 4.5 | 5.6 | 5.3 | | 0.1 |
| | | | 200 | 4 | [d]40.6 | 40.8 | 12.0 | 2.8 | 2.1 | 1.6 | | | |
| | | | | | [h]8 | [d]39.9 | 41.0 | 12.3 | 3.0 | 2.1 | 1.7 | | |
| | | | 200 | R-2 | [e,g]R-4 | 11.7 | 15.0 | 6.6 | 5.9 | 1.3 | 5.9 | 0.2 | 0.1 |
| | | | | | | 39.1[c] | 41.5 | 12.7 | 3.1 | 2.0 | 1.6 | | |

[a]UOP's Y-82 zeolite, NH$_4$F treated, 3 hr, 1/16" E
[b]Recycle feed composition from YES
[c]Recovered catalyst: H$_2$O, 13%; acidity, 0.04 meq/g
[d]Insufficient sample for analysis
[e]Repeat run, collected over 3 hrs, sampled from sight glass
[f]Relative sizes of phases, 1:5.5 (t/b)
[g]Relative sizes of phases, 1:2.9 (t/b)
[h]Similar analyses for repeat sample
[i]From method 27 analysis

TABLE VIII

Recycle Stream Studies
HF/CP316-26 (6798-6)

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE | IPTBE |
| 6834-81 | 6798-6[a] | 50 | | | FS-1 | 25.7 | 36.0 | 11.7 | | 26.5 | | | | |
| | | | 140 | 1 | 1 | 31.4 | 31.3 | 11.5 | 2.1 | 11.7 | 12.0 | 02 | 0.2 | |
| | | | | | 2 | 31.4 | 31.3 | 11.3 | 2.1 | 11.7 | 12.0 | 0.2 | 0.2 | |

TABLE VIII-continued

Recycle Stream Studies
HF/CP316-26 (6798-6)

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | IPTBE |
| | | | 160 | 2 | 3 | 31.9 | 32.2 | 11.5 | 3.8 | 9.8 | 10.6 | 1.0 | 0.2 | 0.12 |
| | | | | | 4 | 32.4 | 32.1 | 11.5 | 3.8 | 9.7 | 10.4 | 1.3 | 0.2 | 0.05 |
| | | | 180 | 3 | 5 | $^c$38.5 | 37.0 | 12.0 | 3.9 | 4.0 | 4.6 | 0.1 | 0.1 | 0.11 |
| | | | | | $^d$6 | $^e$36.4 | 37.4 | 12.1 | 4.3 | 4.9 | 5.0 | 0.1 | 0.1 | |
| | | | | R-1 | $^{e,f}$R-2 | 15.4 | 15.9 | 8.8 | 43.4 | 2.1 | 11.0 | 3.5 | 0.3 | 0.60 |
| | | | | | | 39.0 | 39.4 | 12.3 | 3.1 | 2.9 | 3.3 | 0.1 | 0.1 | |
| | | | 200 | 4 | 7 | $^c$39.0 | 41.5 | 12.7 | 3.0 | 2.1 | 1.6 | | | 0.24 |
| | | | | | $^d$8 | $^e$38.7 | 41.6 | 12.8 | 3.1 | 2.2 | 1.6 | | | 0.48 |
| | | | 200 | R-2 | $^{e,g}$R-4 | 12.2 | 13.2 | 8.4 | 59.3 | 1.0 | 5.1 | 4.1 | 0.1 | 1.16 |
| | | | | | | 41.5$^b$ | 42.0 | 11.1 | 2.3 | 1.9 | 1.1 | 0.1 | | |

$^a$HF treated Valfor CP316-26, 1/16" E
$^b$Recovered catalyst: $H_2O$, 12% Acidity, 0.03 meq/g
$^c$Insufficient sample for analysis
$^d$Similar analyses for repeat sample
$^e$Repeat run, collected over 3 hrs., sampled from sight glass
$^f$Relative sizes of phases, 1:3.3 (t/b)
$^g$Relative sizes of phases, 1:2.9 (t/b)

TABLE IX

Recycle Stream Studies
HF/CP316-26 (6798-6)

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | IPTBE |
| 6834-84 | 6798-3$^a$ | 50 | | | FS-1 | 26.4 | 36.0 | 11.6 | | 25.9 | | | | |
| | | | 140 | 1 | 1 | 30.7 | 32.4 | 11.7 | 2.1 | 12.3 | 10.9 | 0.2 | 0.02 | |
| | | | | | 2 | 30.6 | 32.5 | 11.7 | 2.0 | 12.5 | 10.7 | 0.2 | 0.2 | 0.02 |
| | | | 160 | 2 | 3 | 31.1 | 32.7 | 11.7 | 3.7 | 10.4 | 10.3 | 0.1 | 0.2 | 0.06 |
| | | | | | 4 | 31.5 | 33.0 | 11.8 | 3.7 | 10.3 | 9.9 | 0.1 | 0.2 | 0.05 |
| | | | 180 | 3 | 5 | $^b$34.5 | 36.2 | 11.9 | 5.3 | 6.4 | 5.7 | | 0.2 | 0.03 |
| | | | | | $^d$6 | $^b$33.5 | 35.4 | 11.8 | 5.9 | 7.3 | 6.0 | | 0.2 | 0.03 |
| | | | | R-1 | $^{e,f}$R-2 | 19.7 | 24.2 | 10.0 | 27.6 | 5.6 | 12.7 | 0.1 | 0.5 | 0.05 |
| | | | | | | 34.8 | 35.8 | 11.9 | 4.9 | 6.8 | 5.7 | | 0.1 | 0.04 |
| | | | 200 | | 7 | $^b$37.1 | 38.8 | 12.5 | 3.9 | 1.9 | 3.7 | | 0.1 | 0.02 |
| | | | | | $^d$8 | $^b$34.2 | 36.3 | 11.9 | 5.6 | 6.7 | 5.3 | | 0.1 | 0.01 |
| | | | 200 | R-2 | $^{e,g}$R-4 | 14.6 | 18.2 | 7.4 | 50.8 | 1.6 | 7.2 | | 0.2 | 0.04 |
| | | | | | | 38.1 | 40.5 | 12.9 | 3.4 | 2.6 | 2.3 | | | 0.04 |

$^a$Triflic acid treated SK-500, 1/16" E
$^b$Insufficient sample for analysis
$^c$Recovered catalyst: % $H_2O$, 2.80; Acidity, 0.051 meq/g
$^d$Similar analyses for repeat sample
$^e$Repeat run, collected over 3 hrs., sampled from sight glass
$^f$Relative sizes of phases, 1:7.7 (t/b)
$^g$Relative sizes of phases, 1:3.5 (t/b)

TABLE X

Recycle Stream Studies
HF/SK-500 (6798-4-IR)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE |
| 6834-93 | 6798-4-IR* | 50 | | | FS-1 | 26.2 | 36.2 | 11.6 | | 26.0 | | | |
| | | | 140 | 1 | 1 | 29.8 | 33.2 | 11.6 | 1.8 | 15.2 | 8.3 | | 0.2 |
| | | | | | 2 | 30.0 | 33.1 | 11.7 | 1.9 | 14.8 | 8.5 | | 0.2 |
| | | | 160 | 2 | 3 | 30.7 | 32.9 | 11.7 | 3.3 | 12.0 | 9.3 | | 0.2 |
| | | | | | 4 | 30.7 | 33.1 | 11.8 | 3.2 | 12.3 | 9.0 | | 0.2 |

TABLE X-continued

Recycle Stream Studies
HF/SK-500 (6798-4-IR)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H₂O | MeOH | 2-PrOH | C₄H₈ | tBA | MTBE | C₈H₁₆ | IPTBE |
| | | | 180 | 3 | →5 | 30.5 | 33.1 | 11.5 | 7.8 | 9.3 | 7.6 | | 0.2 |
| | | | | | 6 | 30.7 | 33.6 | 11.7 | 6.4 | 10.3 | 7.2 | | 0.2 |
| | | | | 6 | b,d6-2 | 27.3 | 35.4 | 11.5 | 0.4 | 24.6 | 0.8 | | 0.2 |
| | | | 200 | 4 | →7 | c35.4 | 37.6 | 12.4 | 4.3 | 5.0 | 5.0 | | 0.2 |
| | | | | | 8 | c36.2 | 37.2 | 12.3 | 4.3 | 5.1 | 4.8 | | 0.2 |
| | | | | 5 | →bc8-1 | 8.8 | 14.3 | 7.7 | 49.1 | 3.8 | 15.9 | | |
| | | | | | | 36.0 | 38.0 | 12.4 | 4.0 | 4.8 | 4.8 | | 0.2 |

[a]HF-treated SK-500, 1/16" E
[b]Collected over 3 hrs., sampled from sight glass
[c]Insufficient sample for analysis
[d]Single phase product when in sight glass
[e]Relative sizes of two phases, 1:5.5 (t/b)
[f]Recovered catalyst: % H₂O, 0.66; Acidity, 0.029 meq/g, % °F., 0.39

TABLE XI

Recycle Stream Studies
TF/CP316-26(6798-5)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H₂O | MeOH | 2-PrOH | C₄H₈ | tBA | MTBE | C₈H₁₆ | IPTBE |
| 6834-96 | 6798-5[a] | 50 | | | FS-1 | 26.5 | 36.0 | 11.6 | | 25.9 | | | |
| | | | 140 | 1 | 1 | 31.1 | 32.2 | 11.7 | 2.1 | 11.6 | 11.3 | 0.3 | 0.2 |
| | | | | | 2 | 30.6 | 32.1 | 11.7 | 2.1 | 11.8 | 11.6 | 0.3 | 0.2 |
| | | | 160 | 2 | 3 | 31.9 | 33.3 | 11.8 | 3.9 | 9.4 | 9.4 | 2.0 | 0.2 |
| | | | | | 4 | 31.8 | 33.3 | 11.8 | 3.8 | 9.3 | 10.1 | 1.9 | 0.2 |
| | | | 180 | 3 | 5 | c36.7 | 39.7 | 12.4 | 3.1 | 3.9 | 4.1 | 0.4 | 0.1 |
| | | | | | b,c6 | 16.5 | 20.0 | 9.3 | 39.8 | 2.6 | 11.4 | 5.8 | 0.3 |
| | | | | | | 38.5 | 39.9 | 12.1 | 2.8 | 3.4 | 3.3 | 0.2 | |
| | | | 200 | 4 | 7 | c40.2 | 42.3 | 11.7 | 2.4 | 2.1 | 1.3 | | 0.1 |
| | | | | | b,d8 | 8.9 | 10.8 | 7.1 | 65.5 | 1.0 | 6.0 | 0.1 | 1.1 |
| | | | | | | 39.9 f | 42.3 | 12.0 | 2.6 | 1.9 | 1.3 | | |

[a]Triflic Acid on CP316-26, 1/16" E
[b]Collected over 3 hrs., Sampled from sight glass
[c]Relative sizes of phases, 1:5.0 (t/b)
[d]Relative sizes of phases, 1:3.0 (t/b)
[e]Insufficient sample for analysis
[f]Recovered catalyst: % H₂O, 0.37; Acidity, 0.025 meq/g

TABLE XII

Recycle Stream Studies
HF/CP304-37(6798-7)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H₂O | MeOH | 2-PrOH | C₄H₈ | tBA | MTBE | C₈H₁₆ | IPTBE |
| 6845-11 | 6798-5[a] | 50 | | | FS-1 | 26.3 | 35.7 | 11.7 | | 26.1 | | | |
| | | | 140 | 1 | 1 | 30.6 | 31.8 | 11.7 | 2.1 | 12.6 | 11.2 | 0.1 | 0.2 |
| | | | | | 2 | 30.2 | 31.9 | 11.8 | 2.2 | 12.5 | 11.4 | 0.1 | 0.2 |
| | | | 160 | 2 | 3 | 30.6 | 32.3 | 11.7 | 3.9 | 10.6 | 10.7 | 0.6 | 0.2 |
| | | | | | b4 | 31.2 | 32.5 | 11.8 | 3.9 | 10.2 | 10.3 | 0.5 | 0.2 |
| | | | 180 | 3 | 5 | 32.3 | 34.0 | 11.7 | 6.4 | 8.4 | 6.9 | | 0.2 |
| | | | | | b6 | 30.3 | 33.0 | 11.6 | 7.9 | 9.7 | 7.5 | | 0.2 |

TABLE XII-continued

Recycle Stream Studies
HF/CP304-37(6798-7)

| Run | Catalyst | Feed Rate (cc/hr) | Temp. (°C.) | Time On Stream (Days) | Sample | Product Composition (wt %) Method 26 | | | | | | Method 27 | |
|---|---|---|---|---|---|---|---|---|---|---|---|---|---|
| | | | | | | H₂O | MeOH | 2-PrOH | C₄H₈ | tBA | MTBE | C₈H₁₆ | IPTBE |
| | | | 200 | 4 | 7 | ᶜ37.3 | 39.9 | 12.9 | 3.9 | 3.1 | 2.9 | | |
| | | | | | →ᵇ,ᵈ8 | 14.0 | 18.0 | 7.7 | 48.9 | 2.3 | 9.0 | 0.1 | 0.2 |
| | | | | | | 38.2 | 39.5 | 12.8 | 3.4 | 3.3 | 2.8 | | |
| | | | | | ᵉ | | | | | | | | |

ᵃHF on CP304-37, 1/16" E
ᵇCollected over 3 hrs, sampled from sight glass
ᶜInsufficient Sample for Analysis
ᵈRelative sizes of phases, 1:3.0 (t/b)
ᵉRecovered catalyst: % H₂O, 1.08; Acidity, 0.003 meq/g; % F Fluorine, 0.12

TABLE XIII

Recycle Stream Studies
NH₄F/Y-85(2140-CT-90)

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | H₂O | MeOH | 2-PrOH | C₄H₈ | tBA | MTBE | C₈H₁₆ | IPTBE | DME |
| 6845-15 | 2140-CT-90ᵃ | 50 | | | FS-1 | 26.2 | 35.9 | 11.7 | | 26.2 | | | | |
| | | | 140 | 1 | 1 | 30.5 | 31.8 | 11.7 | 2.0 | 12.9 | 10.8 | 0.1 | 0.2 | 0.01 |
| | | | | | 2 | 29.9 | 32.3 | 11.8 | 2.0 | 13.4 | 10.7 | 0.1 | 0.2 | 0.01 |
| | | | 160 | 2 | 3 | 31.4 | 32.5 | 11.8 | 3.7 | 10.5 | 10.2 | 0.7 | 0.2 | 0.07 |
| | | | | | ᵇ4 | 30.5 | 32.6 | 11.8 | 3.6 | 10.9 | 10.6 | 0.6 | 0.2 | 0.05 |
| | | | 180 | 3 | 5 | ᶜ32.1 | 34.9 | 12.0 | 6.6 | 7.5 | 6.9 | 0.1 | 0.1 | 0.02 |
| | | | | | ᵇ,ᶜ6 | 5.8 | 14.0 | 8.7 | 46.1 | 6.6 | 18.6 | 0.2 | 0.2 | 0.02 |
| | | | | | | 33.3 | 35.5 | 12.0 | 5.6 | 7.2 | 6.4 | | 0.1 | 0.02 |
| | | | 200 | 4 | 7 | ᶜ37.4 | 39.6 | 12.7 | 3.8 | 3.3 | 3.2 | | | 0.02 |
| | | | | | →ᵇ,ᵈ8 | 7.8 | 12.2 | 6.6 | 59.5 | 2.2 | 11.6 | 0.2 | 0.3 | 0.04 |
| | | | | | | 38.3 | 39.4 | 12.8 | 3.3 | 3.2 | 3.1 | | | 0.03 |
| | | | | | ᶠ | | | | | | | | | |

ᵃUOP's Y-84, NH⁴F Treated, 3 hr., 1/16" E
ᵇCollected over 3 hrs, sampled from sight glass
ᶜRelative sizes of phases, 1:12.5 (t/b)
ᵈRelative sizes of phases, 1:33 (t/b)
ᵉInsufficient Sample for Analysis
ᶠRecovered Catalyst: % H₂O, 2.9; Acidity, 0.053 meq/g; % F, 0.18

TABLE XIV

Recycle Stream Studies
TA/SK-500(6798-41)

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | H₂O | MeOH | 2-PrOH | C₄H₈ | tBA | MTBE | C₈H₁₆ | IPTBE | IPTBE |
| 6845-18 | 6798-41ᵃ | 50 | | | FS-1 | 26.4 | 35.8 | 11.7 | | 26.1 | | | | |
| | | | 160 | 1 | 1 | 30.9 | 32.2 | 11.7 | 4.0 | 10.4 | 10.8 | 0.1 | 0.2 | 0.07 |
| | | | | | 2 | 31.4 | 32.3 | 11.8 | 4.2 | 9.9 | 10.4 | 0.1 | 0.2 | 0.07 |
| | | | 180 | 2 | 3 | ᵇ36.9 | 36.8 | 12.2 | 4.2 | 4.8 | 5.2 | | 0.1 | 0.06 |
| | | | | | ᶜ,ᵈ4 | 15.3 | 20.4 | 9.3 | 35.4 | 4.9 | 14.3 | 0.1 | 0.5 | 0.05 |
| | | | | | | 36.2 | 36.2 | 12.1 | 4.7 | 5.3 | 5.6 | | 0.1 | 0.04 |
| | | | 200 | 3 | 5 | ᵇ36.9 | 39.8 | 12.8 | 3.8 | 3.5 | 3.1 | | | 0.02 |
| | | | | | ᶜ,ᶜ6 | 14.3 | 18.6 | 8.2 | 45.2 | 2.9 | 10.7 | | 0.3 | 0.02 |
| | | | | | | 36.9 | 38.8 | 12.6 | 3.9 | 3.9 | 3.8 | | 0.1 | 0.02 |
| | | | | | ᶠ | | | | | | | | | |

TABLE XIV-continued

Recycle Stream Studies
TA/SK-500(6798-41)

| | | Feed Rate | Temp. | Time On Stream | | Product Composition (wt %) Method 26 | | | | | | Method 27 | | |
|---|---|---|---|---|---|---|---|---|---|---|---|---|---|---|
| Run | Catalyst | (cc/hr) | (°C.) | (Days) | Sample | $H_2O$ | MeOH | 2-PrOH | $C_4H_8$ | tBA | MTBE | $C_8H_{16}$ | IPTBE | IPTBE |

[a] Triflic Anhydride on Linde SK-500
[b] Insufficient Sample for Analysis
[c] Collected over 3 hrs., Sampled from sight glass
[d] Relative sizes of phases, 1:6.5 (t/b)
[e] Relative sizes of phases, 1:4.2 (t/b)
[f] Recovered Catalyst: % $H_2O$, 9.6; Acidity, 0.097 meq/g Catalyst Life Studies Two catalyst life studies have been made using the more active of the fluorided zeolites selected from the above screening studies. The chosen catalysts were:

a) The ammonium fluoride-treated LZY-82, sample 2143-CT-90.

b) The HF-modified Y-zeolite CP316-26, sample 6798-6R.

Both runs were made in the same 50 cc capacity, continuous, upflow unit. Selected initial conditions were 200° C., 300 psi, LHSV 2.

Two phase product effluent compositions for run 6845-23 using the 2143-CT-90 catalyst are summarized in Table XV. Typical tBA conversion and MTBE/isobutylene calculated molar selectivities are given in Table III. After an initial break-in period, the DME concentrations dropped to ≦200 ppm, the IPTBE stabilized at ≦0.4% and the diisobutylene content was often below the reliable detectable glc limit. The MTBE concentrations in the reactor effluents are plotted as a function of time on stream in FIG. 1.

The second life test using HF/CP316-26 also successfully completed 2000 hours of service using the simulated second-stage feedstock. Typical two-phase product effluent analyses are given in Table XVI, the tBA conversion data and MTBE, isobutylene molar selectivities are given in Table IV. After an initial break-in period, the diisobutylene and t-butyl isopropyl ether concentrations are typically <1.0% and ≦0.4%, respectively. Dimethyl ether effluent values are in the range 100–200 ppm. In this run the operating temperature was raised to 200° C. after ca. 250 hours on-stream due to a loss of phase separation in sample 6945-67-2.

TABLE XV

Recycle Stream Studies
$NH_4$/LZY-82, Life Study

| | | Feed Rate | Temp. | Time On Stream | | Product Composition (wt %) Method 26 | | | | | | Method 27 | | |
|---|---|---|---|---|---|---|---|---|---|---|---|---|---|---|
| Run | Catalyst | (cc/hr) | (°C.) | (Days) | Sample | $H_2O$ | MeOH | 2-PrOH | $C_4H_8$ | tBA | MTBE | $C_8H_{16}$ | IPTBE | IPTBE |
| 6945-23 | 2143-CT-90[a] | 50 | | | FS-1 | 26.2 | 36.0 | 11.7 | | 26.1 | | | | |
| | | | 200 | 1 | 1[b] | 7.1 | 11.4 | 7.2 | 63.1 | 1.7 | 9.2 | c | c | c |
| | | | | | | 39.7 | 41.6 | 12.5 | 2.9 | 1.9 | 1.4 | | | 0.22 |
| | | | | 2 | →2R[d] | 14.9 | 17.7 | 7.2 | 53.7 | 1.2 | 5.1 | 0.6 | 0.1 | 0.15 |
| | | | | | | 38.6 | 41.8 | 12.8 | 3.0 | 2.1 | 1.6 | | | 0.26 |
| | | | | 4 | 3[e] | 13.7 | 17.2 | 7.2 | 54.1 | 1.5 | 6.2 | 0.2 | 0.2 | 0.07 |
| | | | | | | 38.2 | 41.7 | 13.1 | 3.2 | 2.1 | 1.8 | | | 0.05 |
| | | | | 7 | 4[f] | 11.4 | 14.8 | 6.6 | 58.9 | 1.4 | 6.7 | 0.1 | 0.2 | 0.04 |
| | | | | | | 37.7 | 41.4 | 13.0 | 3.3 | 2.6 | 1.9 | | | 0.04 |
| | | | | 13 | 5[g] | 11.7 | 15.3 | 6.9 | 56.7 | 1.7 | 7.7 | 0.1 | 0.2 | 0.03 |
| | | | | | | 38.0 | 40.6 | 12.9 | 3.5 | 2.8 | 2.2 | | | 0.03 |
| | | | | | FS-2 | 26.1 | 35.6 | 11.6 | | 26.1 | | | | |
| | | | | 17 | →6[h] | 12.6 | 16.6 | 7.2 | 8.8 | 2.0 | 8.8 | 0.1 | 0.2 | 0.02 |
| | | | | | | 38.0 | 40.1 | 12.8 | 3.4 | 3.0 | 2.7 | | | 0.02 |
| | | | | [i]20 | →7 | 31.2 | 33.9 | 11.7 | 6.9 | 9.7 | 6.5 | | 0.2 | 0.01 |
| | | | | 25 | 8 | 30.1 | 34.4 | 11.7 | 5.4 | 12.7 | 5.7 | | 0.2 | |
| | | | | j | FS-3 | 26.2 | 35.7 | 12.1 | | 25.9 | | | | |
| | | | 220[j] | 28 | 9[k] | 17.1 | 20.9 | 8.6 | 41.7 | 2.9 | 8.7 | 0.7 | 0.3 | 0.02 |
| | | | | | | 37.2 | 39.0 | 12.9 | 3.8 | 3.9 | 3.2 | 0.1 | | 0.02 |
| | | | | 31 | 10[i] | 13.9 | 17.8 | 7.8 | 49.7 | 2.3 | 8.4 | 0.1 | 0.2 | 0.01 |
| | | | | | | 35.0 | 38.7 | 15.8 | 3.9 | 3.9 | 2.7 | | | 0.01 |
| 6945-23 | 214-CT-90 | 50 | 220 | 35 | 11[k] | 3.0 | 6.8 | 5.3 | 70.6 | 2.0 | 12.2 | 0.1 | 0.3 | 0.02 |
| | | | | | | 40.2 | 38.9 | 12.4 | 2.8 | 3.2 | 2.5 | | | 0.01 |
| | | | | | FS-4 | 26.4 | 35.8 | 11.7 | | 26.1 | | | | 0.07 |
| | | | | 38 | 12[l] | 17.7 | 20.9 | 8.1 | 44.2 | 2.0 | 6.9 | 0.1 | 0.2 | 0.02 |
| | | | | | | 38.1 | 40.8 | 12.5 | 3.2 | 3.0 | 2.3 | | | 0.01 |
| | | | | 46 | 13[m] | 10.5 | 13.9 | 6.4 | 60.8 | 1.4 | 6.8 | | | |
| | | | | | | 37.7 | 41.4 | 13.0 | 3.5 | 2.4 | 2.0 | 0.1 | | 0.01 |
| | | | | | FS-5 | 26.2 | 36.0 | 11.7 | | 26.1 | | | | |

TABLE XV-continued

Recycle Stream Studies
$NH_4/LZY-82$, Life Study

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | IPTBE |
| | | | | 52 | →14[l] | 11.8 | 15.4 | 6.6 | 57.9 | 1.4 | 6.7 | 0.1 | | 0.02 |
| | | | | | | 38.0 | 41.1 | 13.0 | 3.3 | 2.3 | 2.0 | | | 0.01 |
| | | | | 60 | 15[l] | 5.3 | 9.5 | 5.3 | 70.2 | 1.4 | 8.2 | 0.1 | 0.2 | 0.02 |
| | | | | | | 31.7 | 46.0 | 13.5 | 4.2 | 3.0 | 1.6 | | | 0.01 |
| | | | | 66 | 16[o] | 1.4 | 5.0 | 4.1 | 80.3 | 1.0 | 7.8 | | 0.1 | 0.02 |
| | | | | | | 34.8 | 42.6 | 13.1 | 4.4 | 2.5 | 2.6 | | | 0.01 |
| | | | | | FS-6 | 26.4 | 36.2 | 11.5 | | 25.8 | | | | |
| | | | | | | 26.4 | 36.1 | 11.5 | | 25.8 | | | | |
| | | | | 74 | 17[n] | 5.7 | 12.7 | 7.2 | 56.1 | 4.4 | 13.7 | | 0.4 | 0.01 |
| | | | | | | 32.3 | 38.3 | 12.4 | 6.3 | 5.9 | 4.8 | | 0.1 | 0.01 |
| | | | | 81 | 18[o] | 3.4 | 9.1 | 6.3 | 63.4 | 3.4 | 142 | | 0.4 | 0.01 |
| | | | | | | 35.4 | 38.4 | 12.3 | 4.9 | 4.8 | 4.1 | | 0.1 | 0.01 |
| | | | | 84 | 19[n] | 4.0 | 9.9 | 6.6 | 61.3 | 3.9 | 14.1 | | 0.4 | |
| | | | | | p,q | 35.0 | 38.3 | 12.2 | 5.1 | 5.3 | 4.1 | | 0.1 | |

[a]UOP's Y-82 Zeolite, $NH_4F$ Treated, 6 hrs., 1/16" E
[b]No data on relative volumes of the two phases
[c]No glc analyses data
[d]Relative sizes of phases, 1:2.8 (t/b)
[e]Relative sizes of phases, 1:3.2 (t/b)
[f]Relative sizes of phases, 1:3.5 (t/b)
[g]Relative sizes of phases, 1:3.9 (t/b)
[h]Relative sizes of phases, 1:3.5 (t/b)
[i]ARL power outage, unit shut down
[j]Raise Operating temperature
[l]Relative sizes of phases 1:3.5 (t/b)
[k]Relative sizes of phases 1:3.8 (t:b)
[m]Relative sizes of phases 1:3.4 (t/b)
[n]Relative sizes of phases 1:5.4 (t/b)
[o]Relative sizes of phases 1:4.4 (t/b)
[p]Recovered catalyst: % $H_2O$, 1.88; % F, 8050 ppm; Acidity, 0.009 meq/g
[q]Fine: % $H_2O$, 1.93; % F, 2.3 Acidity 0.006 meq/g

TABLE XVI

Recycle Stream Studies
$NH_4/LZY-82$, Life Study

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | IPTBE |
| 6945-67 | 6798-6R[a] | 50 | | | FS-1 | 26.4 | 36.2 | 11.5 | | 25.8 | | | | |
| | | | 200 | 1 | →1[b] | 24.5 | 26.1 | 9.6 | 34.0 | 1.5 | 3.8 | 3.0 | 0.1 | 0.80 |
| | | | | | | 39.0 | 42.7 | 11.8 | 3.1 | 1.8 | 1.5 | | | 0.58 |
| | | | | 8 | 2 | 31.0 | 35.2 | 11.6 | 7.8 | 9.1 | 5.3 | 0.1 | 0.1 | |
| | | | | | FS-2 | 26.4 | 36.1 | 11.5 | | 25.8 | | | | |
| | | | [c]220 | 15 | 3[d] | 7.8 | 12.8 | 6.6 | 60.1 | 3.1 | 9.5 | 0.1 | 0.3 | 0.02 |
| | | | | | | 36.0 | 39.4 | 12.4 | 4.6 | 4.6 | 2.8 | | | 0.01 |
| | | | | 19 | →4[e] | 1.2 | 7.0 | 5.8 | 69.8 | 3.3 | 12.5 | | 0.3 | 0.02 |
| | | | | | | 35.6 | 39.1 | 12.4 | 4.9 | 4.9 | 3.1 | | 0.1 | 0.01 |
| | | | | 24 | 5[f] | 5.4 | 13.4 | 7.3 | 57.5 | 4.9 | 11.4 | | 0.3 | 0.01 |
| | | | | | | 28.4 | 38.5 | 12.7 | 8.7 | 6.9 | 4.7 | | 0.1 | 0.01 |
| | | | | 31 | 6[g] | 6.6 | 11.3 | 7.6 | 53.8 | 5.6 | 13.1 | | 0.4 | 0.01 |
| | | | | | | 34.1 | 37.3 | 12.1 | 5.5 | 6.8 | 4.1 | | 0.1 | 0.01 |
| | | | | | FS-3 | 26.0 | 36.3 | 11.6 | | 26.0 | | | | |
| | | | | 38 | 7[h] | 3.4 | 8.1 | 5.4 | 70.4 | 2.4 | 9.9 | | 0.2 | 0.01 |
| | | | | | | 33.8 | 41.6 | 13.1 | 4.5 | 4.1 | 2.8 | | | 0.01 |
| | | | | | FS-4 | 26.5 | 35.6 | 11.4 | | 26.4 | | | | |
| | | | | 45 | 8[i] | 1.4 | 6.6 | 5.5 | 70.6 | 3.4 | 12.1 | | 0.2 | 0.01 |
| | | | | | | 31.8 | 40.7 | 13.2 | 4.8 | 6.2 | 3,2 | | | 0.01 |
| 6945-67 | 6798-6R | 50 | 220 | | FS-51 | 26.5 | 35.8 | 11.6 | | 26.0 | | | | |
| | | | | 53 | →9[j] | 3.0 | 92 | 6.3 | 64.0 | 4.0 | 13.4 | | 0.2 | 0.01 |
| | | | | | | 33.8 | 38.4 | 12.1 | 5.9 | 5.4 | 4.4 | | | 0.01 |
| | | | | 57 | 10 | 3.2 | 9.5 | 6.6 | 62.7 | 4.6 | 13.4 | | | 0.01 |
| | | | | | | 32.8 | 37.3 | 12.1 | 6.5 | 6.9 | 4.0 | | | 0.01 |
| | | | | | FS-6 | 26.4 | 36.1 | 11.6 | | 25.8 | | | | |

TABLE XVI-continued

Recycle Stream Studies
NH$_4$/LZY-82, Life Study

| Run | Catalyst | Feed Rate (cc/hr) | Temp. (°C.) | Time On Stream (Days) | Sample | Product Composition (wt %) Method 26 | | | | | | Method 27 | | |
|---|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE | IPTBE |
| | | | | 68 | 11$^g$ | $^l$33.5 | 36.3 | 11.9 | 6.2 | 7.4 | 4.4 | | 0.4 | 0.01 |
| | | | | 72 | 12$^k$ | 18.9 | 24.3 | 9.7 | 30.4 | 7.4 | 9.1 | | 0.4 | 0.01 |
| | | | | | | 33.0 | 35.8 | 11.8 | 6.6 | 7.9 | 4.5 | | | 0 |
| | | | | | FS=7 | 26.4 | 35.7 | 11.5 | | | 25.8 | | | |
| | | | | 78 | 13$^m$ | 3.6 | 10.1 | 6.7 | 60.6 | 4.9 | 14.0 | | 0.3 | 0.01 |
| | | | | | | 34.4 | 37.1 | 12.0 | 5.6 | 6.3 | 4.1 | | 0.1 | |
| | | | | 85 | 14$^n$ | 1.7 | 7.5 | 5.8 | 69.6 | 3.5 | 11.2 | | 0.2 | 0.01 |
| | | | | | | 35.0 | 37.9 | 12.1 | 6.0 | 5.5 | 2.9 | | | 0.01 |
| | | | | | o | | | | | | | | | |

$^a$HF Treated CP316-26, 1/16" E, Dried at 240° C.
$^b$Relative sizes of phases 1:3.0 (t/b)
$^c$Raise operating temperature
$^d$Relative sizes of phases, 1:4.4 (t/b)
$^e$Relative sizes of phases, 1:5.2 (t/b)
$^f$Relative sizes of phases, 1:2.2 (t/b)
$^g$Relative sizes of phases, 1:7.3 (t/b)
$^h$Relative sizes of phases, 1:4.0 (t/b)
$^i$Relative sizes of phases, 1:4.6 (t/b)
$^j$Relative sizes of phases, 1:6.1 (t/b)
$^k$Relative sizes of phases, 1:14.1 (t/b)
$^l$Sample lost during analysis
$^m$Relative sizes of phases, 1:8.1 (t/b)
$^n$Relative sizes of phases, 1:8.2 (t/b)
$^o$Recovered catalyst: % H$_2$O, 1.21; % F, 0.7; Acidity, 0.01 meq/g

We claim:

1. A method for the preparation of methyl tertiary butyl ether (MTBE) from tertiary butyl alcohol (TBA) and methanol (MeOH) in three stages which comprises the steps of:

a) charging a reaction feed mixture comprising methanol and tertiary butyl alcohol to a primary MTBE reaction zone containing a bed of a cationic ion-exchange resins catalyst and reacting the reaction feed mixture therein to form a primary etherification reaction product comprising unreacted methanol, unreacted tertiary butyl alcohol, water, isobutylene and methyl tertiary butyl ether, b) charging the primary reaction product to a first methyl tertiary butyl ether distillation zone and separating it therein into a first lighter distillation fraction comprising isobutylene, methanol and methyl tertiary butyl ether and a first heavier distillation fraction comprising methanol, tertiary butyl alcohol and water, c) charging the first heavier distillation fraction to a second stage MTBE reaction zone containing a bed of a fluoride-treated strongly acidic Y-zeolite or a fluoride-treated silicoaluminophosphate (SAPO) molecular sieves operated under conversion conditions including a temperature of from 20° to 300° C. and a pressure of from 0 to 1000 psig to form a second stage etherification reaction product comprising primarily isobutylene and about 6 to about 13 mol % methyl tertiary butyl ether, and also containing unreacted tertiary butyl alcohol, methanol and water, d) charging the second stage reaction product to a second methyl tertiary butyl ether distillation zone and fractionating it therein to provide a second lighter distillation fraction comprising methanol, tertiary butyl alcohol, isobutylene and methyl tertiary butyl ether, and a second heavier distillation fraction comprising water, e) charging the first lower boiling (lighter) distillation fraction and an isobutylene conversion product to a methanol solvent extraction zone and countercurrently contacting them therein with water to provide an overhead extract comprising isobutylene, water and methyl tertiary butyl ether and a raffinate comprising methanol, MTBE, isobutylene, dimethyl ether and water;

f). charging the extract to a third isobutylene distillation zone and separating it therein into a third lower boiling (lighter) distillation fraction comprising water, a third intermediate boiling fraction comprising isobutylene and a third higher boiling (heavier) distillation fraction comprising methyl tertiary butyl ether;

g). charging at least a portion of the third intermediate isobutylene fraction and added methanol to an isobutylene conversion reaction zone containing a bed of a cationic ion-exchange resin catalyst and reacting the reaction feed mixture therein to thereby convert the charged methanol and isobutylene to methyl tertiary butyl ether and form an isobutylene conversion product comprising methyl tertiary butyl ether, isobutylene, methanol, tertiary butyl alcohol and water; and h). recycling said isobutylene conversion product to said methanol solvent extraction zone.

i), the fluoride treated strongly acidic Y-zeolite having a silica/alumina ratio of about 100:1 to about 10:1 and a unit cell size of 24.20 to 24.45 A; and j). the fluoride-treated silicoaluminaphosphate having a pore size of from 5 to 9 A, and being selected from the group consisting of SAPO-37 and SAPO-5, SAPO-11 and SAPO-31.

2. The composition of claim 1 wherein the Y-zeolite consists essentially of a Y-zeolite having a Si:Al ratio of 1.5–2.5 contacted with hydrofluoric acid.

3. The composition of claim 1 wherein the Y-zeolite consists essentially of a Y-zeolite having a Si:Al ratio of about 46:1 contacted with hydrofluoric acid.

4. A method for the preparation of methyl tertiary butyl ether (MTBE) from tertiary butyl alcohol (TBA) and methanol (MeOH) in three stages which comprises the steps of:

a) charging a reaction feed mixture comprising methanol and tertiary butyl alcohol to a primary MTBE reaction zone containing a bed of a cationic ion-exchange resin catalyst and reacting the reaction feed mixture therein to form a primary etherification reaction product comprising unreacted methanol, unreacted tertiary butyl alcohol, water, isobutylene and methyl tertiary butyl ether, b) charging the primary reaction product to a first methyl tertiary butyl ether distillation zone and separating it therein into a first lighter distillation fraction comprising isobutylene, methanol and methyl tertiary butyl ether and a first heavier distillation fraction comprising methanol, tertiary butyl alcohol and water, c) charging the first heavier distillation fraction to a second stage MTBE reaction zone containing a bed of a fluoride-treated Y-zeolite or a fluoride-treated silicoaluminophosphate (SAPO) molecular sieve operated under conversion conditions including a temperature of 160° to 240° C. and a pressure of 50 to 500 psig. selected to convert at least 80 wt. % of the tertiary; butyl alcohol so as to form a second stage two-phase etherification reaction product comprising primarily isobutylene and about 6 to about 13 mol % methyl tertiary butyl ether, and also containing unreacted tertiary butyl alcohol, methanol and water, d) charging the second stage reaction product to a separation drum and separating it therein into a lighter supernatant fraction comprising tertiary butyl alcohol, isobutylene and methyl tertiary butyl alcohol and a heavier aqueous fraction comprising methanol and water, e) charging the first lower boiling (lighter) distillation fraction, an isobutylene conversion product and the heavier aqueous fraction to a methanol solvent extraction zone and countercurrently contacting them therein with water to provide an overhead extract comprising isobutylene, water and methyl tertiary butyl ether and a raffinate comprising methanol, MTBE, isobutylene, dimethyl ether and water;

f) charging the extract to a third isobutylene distillation zone and separating it therein into a third lower boiling (lighter) distillation fraction comprising water, a third intermediate boiling fraction comprising isobutylene and a third higher boiling (heavier) distillation fraction comprising methyl tertiary butyl ether;

g). charging the third intermediate isobutylene fraction, the lighter supernatant fraction and added methanol to an isobutylene conversion reaction zone containing a bed of a cationic ion-exchange resin catalyst and reacting the reaction feed mixture therein to thereby convert the charged methanol and isobutylene to methyl tertiary butyl ether and form an isobutylene conversion product comprising methyl tertiary butyl ether, isobutylene, methanol, tertiary butyl alcohol and water; and h). recycling said isobutylene conversion product to said methanol solvent extraction zone.

i), the fluoride treated strongly acidic Y-zeolite having a silica/alumina ratio of about 100:1 to about 10:1 and a unit cell size of 24.20 to 24.45 A; and j). the fluoride-treated silicoaluminaphosphate having a pore size of from 5 to 9 A, and being selected from the group consisting of SAPO-37 and SAPO-5, SAPO-11 and SAPO-31.

* * * * *